(12) United States Patent
Smith et al.

(10) Patent No.: US 11,768,182 B2
(45) Date of Patent: Sep. 26, 2023

(54) PHOTOACOUSTIC AND OPTICAL MICROSCOPY COMBINER AND METHOD OF GENERATING A PHOTOACOUSTIC IMAGE OF A SAMPLE

(71) Applicants: Barbara S. Smith, Scottsdale, AZ (US); Christopher Miranda, Tempe, AZ (US); Ethan B. Marschall, Queen Creek, AZ (US)

(72) Inventors: Barbara S. Smith, Scottsdale, AZ (US); Christopher Miranda, Tempe, AZ (US); Ethan B. Marschall, Queen Creek, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 523 days.

(21) Appl. No.: 16/859,633

(22) Filed: Apr. 27, 2020

(65) Prior Publication Data

US 2020/0340954 A1 Oct. 29, 2020

Related U.S. Application Data

(60) Provisional application No. 62/839,604, filed on Apr. 26, 2019.

(51) Int. Cl.
*G01N 21/17* (2006.01)
*G01N 29/24* (2006.01)
(Continued)

(52) U.S. Cl.
CPC ....... *G01N 29/2418* (2013.01); *A61B 5/0095* (2013.01); *G01N 21/1702* (2013.01);
(Continued)

(58) Field of Classification Search
CPC ........... G01N 21/1702; G01N 29/2418; G01N 29/2425; G01N 29/221; A61B 5/0095; G02F 1/33; G02F 1/332; G02F 1/335
See application file for complete search history.

(56) References Cited

U.S. PATENT DOCUMENTS 4,267,732 A * 5/1981 Quate ................... G01H 3/125
73/606
5,752,518 A 5/1998 Mcgee et al.
(Continued)

FOREIGN PATENT DOCUMENTS

CN 2061692 U 9/1990
FR 2997502 A1 5/2014
(Continued)

OTHER PUBLICATIONS

United States Patent Office Action for U.S. Appl. No. 16/159,167 dated Mar. 23, 2021 (15 pages).
(Continued)

*Primary Examiner* — Herbert K Roberts
(74) *Attorney, Agent, or Firm* — Michael Best & Friedrich LLP

(57) ABSTRACT

A photoacoustic and optical microscopy combiner. The combiner is configured to support a transducer defining an axis. The combiner includes a body including a base and an opening extending through the base, and a glass member at least partially positioned within the opening. The glass member includes a surface positioned at an angle relative to the base and the axis of the transducer. A sample slide is supported on the body and at least partially over the opening. The sample slide is positioned such that a sample on the sample slide is configured to receive light from a laser and redirect the light to an ultrasound transducer to generate a real-time image of a sample.

9 Claims, 11 Drawing Sheets

(51) Int. Cl.
  *A61B 5/00* (2006.01)
  *G02B 21/00* (2006.01)
  *G01N 29/22* (2006.01)
(52) U.S. Cl.
  CPC ....... *G01N 29/221* (2013.01); *G02B 21/0004* (2013.01); *G01N 2291/106* (2013.01)

(56) References Cited

U.S. PATENT DOCUMENTS

| | | | |
|---|---|---|---|
| 8,932,223 | B2 | 1/2015 | Emelianov et al. |
| 9,618,445 | B2* | 4/2017 | Sun .................... G01N 29/2418 |
| 10,107,613 | B2 | 10/2018 | Jiao et al. |
| 10,795,440 | B1 | 10/2020 | Chevillet et al. |
| 2007/0299341 | A1* | 12/2007 | Wang .................. A61B 5/0093 600/443 |
| 2010/0079580 | A1* | 4/2010 | Waring, IV .......... H04N 13/111 348/E13.001 |
| 2010/0245766 | A1 | 9/2010 | Zhang et al. |
| 2011/0098530 | A1 | 4/2011 | Yamane |
| 2011/0282192 | A1 | 11/2011 | Axelrod et al. |
| 2011/0301458 | A1 | 12/2011 | Li et al. |
| 2012/0275262 | A1* | 11/2012 | Song .................. G01N 29/2418 367/7 |
| 2013/0158383 | A1* | 6/2013 | Cheng ................. A61B 5/0095 600/407 |
| 2013/0216114 | A1 | 8/2013 | Courtney et al. |
| 2014/0066743 | A1* | 3/2014 | Nakajima ............ A61B 5/0095 600/407 |
| 2014/0142404 | A1 | 5/2014 | Wang et al. |
| 2015/0160168 | A1 | 6/2015 | Irisawa |
| 2015/0226845 | A1* | 8/2015 | Witte ................. G01N 21/1702 367/87 |
| 2015/0247999 | A1* | 9/2015 | Ntziachristos ..... G01N 21/1702 348/80 |
| 2015/0327768 | A1 | 11/2015 | Oyama et al. |
| 2016/0003777 | A1* | 1/2016 | Schmitt-Manderbach ................... G01N 29/44 73/606 |
| 2016/0143542 | A1* | 5/2016 | Bossy .................... A61B 1/042 600/407 |
| 2016/0242651 | A1* | 8/2016 | Wang .................. A61B 5/6868 |
| 2016/0249812 | A1* | 9/2016 | Wang ................. G01N 29/0681 600/407 |
| 2016/0250073 | A1* | 9/2016 | Gooding ............. A61F 9/00802 606/6 |
| 2016/0305914 | A1* | 10/2016 | Wang .................... G02B 21/008 |
| 2016/0356746 | A1* | 12/2016 | Piestun ............. G01N 29/0654 |
| 2017/0055841 | A1 | 3/2017 | Mueller et al. |
| 2017/0065182 | A1* | 3/2017 | Wang .................. A61B 5/0095 |
| 2017/0105626 | A1 | 4/2017 | Irisawa |
| 2017/0156600 | A1* | 6/2017 | Ntziachristos ....... A61B 5/0077 |
| 2017/0367682 | A1 | 12/2017 | Smith et al. |
| 2018/0055343 | A1 | 3/2018 | Yang et al. |
| 2018/0078143 | A1* | 3/2018 | Pramanik ............ A61B 5/0073 |
| 2018/0132728 | A1* | 5/2018 | Wang .................. A61B 5/0095 |
| 2018/0214119 | A1 | 8/2018 | Mehrmohammadi et al. |
| 2018/0235570 | A1 | 8/2018 | Fukushima |
| 2019/0046159 | A1 | 2/2019 | Smith et al. |
| 2019/0110691 | A1 | 4/2019 | Smith et al. |
| 2019/0175938 | A1 | 6/2019 | Rezaie et al. |
| 2019/0227038 | A1* | 7/2019 | Wang .................... G02B 21/36 |
| 2019/0282069 | A1 | 9/2019 | Smith et al. |
| 2020/0056986 | A1* | 2/2020 | Wang ................. G01N 21/1702 |
| 2020/0160522 | A1 | 5/2020 | Merlo et al. |
| 2020/0173965 | A1* | 6/2020 | Sangu ................ G02B 17/061 |
| 2020/0398268 | A1 | 12/2020 | Smith et al. |
| 2021/0080708 | A1* | 3/2021 | Sangu ................ G02B 17/0808 |
| 2022/0151496 | A1* | 5/2022 | Waldner ............... A61B 5/4519 |

FOREIGN PATENT DOCUMENTS

| | | |
|---|---|---|
| IN | 308501 B | 4/2019 |
| WO | WO2008075299 A1 | 6/2008 |
| WO | WO2008100386 A2 | 8/2008 |
| WO | 2009050632 A1 | 4/2009 |
| WO | WO2015175431 A1 | 11/2015 |
| WO | 2015183092 A1 | 12/2015 |

OTHER PUBLICATIONS

Knight et al., "Hollow-Core Optical Fibers Offer Advantages at Any Wavelength," Photonics Spectra, Apr. 2019.
Abbas, J. J.; Smith, B.; Poluta, M.; Velazquez-Berumen, A., Improving health-care delivery in lowresource settings with nanotechnology:Challenges in multiple dimensions. Nanobiomedicine 2017, 4, 1849543517701158.
Abe, Y.-W. Shi, Y. Matsuura, and M. Miyagi, "Flexible small-bore hollow fibers with an inner polymer coating," Opt. letters 25, 150-152 (2000).
Addington, CP, Dharmaraj, S, Heffernan, JM, Sirianni, RW, Stabenfeldt, SE. Hyaluronic acid-laminin hydrogels increase neural stem cell transplant retention and migratory response to SDF-1α. Matrix Biology. 2017, 60-61, 206-216.
Anand, S.; Kumar, S. S.; Muthuswamy, J., Autonomous control for mechanically stable navigation of microscale implants in brain tissue to record neural activity. Biomedical Microdevices 2016, 18 (4).
Anderson, T. R.; Hu, B.; Iremonger, K.; Kiss, Z. H. T., Selective attenuation of afferent synaptic transmission as a mechanism of thalamic deep brain stimulation-induced tremor arrest. Journal of Neuroscience 2006, 26 (3), 841-850.
Anderson, T. R.; Huguenard, J. R.; Prince, D. A., Differential effects of Na plus -K plus ATPase blockade on cortical layer V neurons. Journal of Physiology—London 2010, 588 (22), 4401-4414.
Andrasfalvy, B. K.; Galinanes, G. L.; Huber, D.; Barbic, M.; Macklin, J. J.; Susumu, K.; Delehanty, J. B.; Huston, A. L.; Makara, J. K.; Medintz, I. L., Quantum dot-based multiphoton fluorescent pipettes for targeted neuronal electrophysiology. Nat. Methods 2014, 11 (12), 1237-1241.
Annecchino, A. R. Morris, C. S. Copeland, O. E. Agabi, P. Chadderton, and S. R. Schultz, "Robotic automation of in vivo two-photon targeted whole-cell patch-clamp electrophysiology," Neuron 95, 1048-1055 (2017).
Aravanis, A. M.; Wang, L. P.; Zhang, F.; Meltzer, L. A.; Mogri, M. Z.; Schneider, M. B.; Deisseroth, K., An optical neural interface: in vivo control of rodent motor cortex with integrated fiberoptic and optogenetic technology. Journal of Neural Engineering 2007, 4 (3), S143-S156.
Aston-Jones, G.; Deisseroth, K., Recent advances in optogenetics and pharmacogenetics. Brain Research 2013, 1511, 1-5.
Badu-Tawiah, A. K.; Lathwal, S.; Kaastrup, K.; Al-Sayah, M.; Christodouleas, D. C.; Smith, B. S.; Whitesides, G. M.; Sikes, H. D., Polymerization-based signal amplification for paper-based immunoassays. Lab on a chip 2015, 15 (3), 655-659.
Balaic, D. X.; Nugent, K. A., x-ray optics of tapered capillaries. Applied Optics 1995, 34 (31), 7263-7272.
Beard, P., Biomedical photoacoustic imaging. Interface Focus 2011, 1 (4), 602-631.
Beaulieu-Laroche, L.; Harnett, M. T., Dendritic Spines Prevent Synaptic Voltage Clamp. Neuron 2018, 97 (1), 75-82.
Bilderback, D. H.; Fontes, E., Glass capillary optics for making x-ray beams of 0.1 to 50 microns diameter. AIP Conference Proceedings 1997, Medium: X; Size: pp. 147-155.
Billet, A.; Froux, L.; Hanrahan, J. W.; Becq, F., Development of Automated Patch Clamp Technique to Investigate CFTR Chloride Channel Function. Frontiers in Pharmacology 2017, 8.
Bohndiek, S. Bodapati, D. Van De Sompel, S.-R. Kothapalli, and S. S. Gambhir, "Development and application of stable phantoms for the evaluation of photoacoustic imaging instruments," PloS one 8, e75533 (2013).
Bornstein, J. C.; Furness, J. B., correlated electrophysiological and histochemical-studies of submucous neurons and their contribution to understanding enteric neural circuits. Journal of the Autonomic Nervous System 1988, 25 (1), 1-13.

(56) References Cited

OTHER PUBLICATIONS

Boyden, E. S.; Zhang, F.; Bamberg, E.; Nagel, G.; Deisseroth, K., Millisecond-timescale, genetically targeted optical control of neural activity. Nature Neuroscience 2005, 8 (9), 1263-1268.
Chen, C. C.; Cang, C. L.; Fenske, S.; Butz, E.; Chao, Y. K.; Biel, M.; Ren, D. J.; Wahl-Schott, C.; Grimm, C., Patch-clamp technique to characterize ion channels in enlarged individual endolysosomes. Nat. Protoc. 2017, 12 (8), 1639-1658.
Cox, B.; Laufer, J. G.; Arridge, S. R.; Beard, P. C., Quantitative spectroscopic photoacoustic imaging: a review. J. Biomed. Opt. 2012, 17 (6).
Cullen, D. K.; Stabenfeldt, S. E.; Simon, C. M.; Tate, C. C.; LaPlaca, M. C., In vitro neural injury model for optimization of tissue-engineered constructs. Journal of Neuroscience Research 2007, 85 (16), 3642-3651.
De La Zerda, Adam, et al. "Carbon nanotubes as photoacoustic molecular imaging agents in living mice." Nature nanotechnology 3.9 (2008): 557.
Deisseroth, K., Optogenetics. Nat. Methods 2011, 8 (1), 26-29.
Desai, N. S.; Siegel, J. J.; Taylor, W.; Chitwood, R. A.; Johnston, D., MATLAB-based automated patch-clamp system for awake behaving mice. Journal of Neurophysiology 2015, 114 (2), 1331-1345.
Dika et al., Early experiences and integration in the persistence of first-generation college students in STEM and non-STEM majors. Journal of Research in Science Teaching 2016, 53 (3), 368-383.
Dunn, R. C., Near-field scanning optical microscopy. Chemical reviews 1999, 99 (10), 2891-2928.
Fan, B.; Li, W., Miniaturized optogenetic neural implants: a review. Lab on a Chip 2015, 15 (19), 3838-3855.
Fenno, L.; Yizhar, O.; Deisseroth, K., The Development and Application of Optogenetics. In Annual Review of Neuroscience, vol. 34, Hyman, S. E.; Jessell, T. M.; Shatz, C. J.; Stevens, C. F.; Zoghbi, H. Y., Eds. 2011; vol. 34, pp. 389-412.
Frow, E. K.; Smith, B. S.; Ankeny, C. J. In Freshman design course: Device design for low-resource settings, ASEE Annual Conference and Exposition, Conference Proceedings, 2017.
Galanzha, E. I.; Shashkov, E. V.; Spring, P. M.; Suen, J. Y.; Zharov, V. P., In vivo, Noninvasive, Label-Free Detection and Eradication of Circulating Metastatic Melanoma Cells Using Two-Color Photoacoustic Flow Cytometry with a Diode Laser. Cancer Research 2009, 69 (20), 7926-7934.
Goddeyne, C.; Nichols, J.; Wu, C.; Anderson, T., Repetitive mild traumatic brain injury induces ventriculomegaly and cortical thinning in juvenile rats. Journal of Neurophysiology 2015, 113 (9), 3268-3280.
Gooch, C. L.; Pracht, E.; Borenstein, A. R., The burden of neurological disease in the United States: A summary report and call to action. Annals of neurology 2017, 81 (4), 479-484.
Grewe, B. F.; Langer, D.; Kasper, H.; Kampa, B. M.; Helmchen, F., High-speed in vivo calcium imaging reveals neuronal network activity with near-millisecond precision (vol. 7, p. 399, 2010). Nat. Methods 2010, 7 (6), 479-479.
Hamill, O. P.; Marty, A.; Neher, E.; Sakmann, B.; Sigworth, F. J., improved patch-clamp techniques for high-resolution current recording from cells and cell-free membrane patches. Pflugers Arch. 1981, 391 (2), 85-100.
Harvey, C. D.; Collman, F.; Dombeck, D. A.; Tank, D. W., Intracellular dynamics of hippocampal place cells during virtual navigation. Nature 2009, 461 (7266), 941-U196.
Hayar, C. Gu, and E. D. Al-Chaer, "An improved method for patch clamp recording and calcium imaging of neurons in the intact dorsal root ganglion in rats," J. neuroscience methods 173, 74-82 (2008).
Hecht, B.; Sick, B.; Wild, U. P.; Deckert, V.; Zenobi, R.; Martin, O. J. F.; Pohl, D. W., Scanning near-field optical microscopy with aperture probes: Fundamentals and applications. Journal of Chemical Physics 2000, 112 (18), 7761-7774.
Helmchen, F.; Denk, W., Deep tissue two-photon microscopy. Nat. Methods 2005, 2 (12), 932-940.
Hu, S.; Maslov, K.; Wang, L. V., Second-generation optical-resolution photoacoustic microscopy with improved sensitivity and speed. Opt. Lett. 2011, 36 (7), 1134-1136.
Hurtado, S.; Newman, C. B.; Tran, M. C.; Chang, M. J., Improving the Rate of Success for Underrepresented Racial Minorities in STEM Fields: Insights from a National Project. New Directions for Institutional Research 2010, 148, 5-15.
Ishitani, T. T., Studying attrition and degree completion behavior among first-generation college students in the United States. The Journal of Higher Education 2006, 77 (5), 861-885.
Jansen, M. Wu, A. F. van der Steen, and G. van Soest, "Lipid detection in atherosclerotic human coronaries by spectroscopic intravascular photoacoustic imaging," Opt. express 21, 21472-21484 (2013).
Karpiouk, B. Wang, J. Amirian, R. W. Smalling, and S. Y. Emelianov, "Feasibility of in vivo intravascular photoacoustic imaging using integrated ultrasound and photoacoustic imaging catheter," J. biomedical optics 17, 0960081-0960086 (2012).
Keene, A. C.; Waddell, S., *Drosophila* olfactory memory: single genes to complex neural circuits. Nature Reviews Neuroscience 2007, 8 (5), 341-354.
Khraiche, W Phillips*, N Jackson*, J Muthuswamy, "Sustained Elevation of Activity of Developing Neurons Grown on Polyamide Microelectrode Arrays (MEA) in Response to Ultrasound Exposure," Microsystem Technologies, 2017, 23:3671-3683.
Kim, E. Chung, H. Yamashita, K. E. Hung, A. Mizoguchi, R. Kucherlapati, D. Fukumura, R. K. Jain, and S. H. Yun, "In vivo wide-area cellular imaging by side-view endomicroscopy," Nat. methods 7, 303 (2010).
Kim, Taeho et al. "Photoacoustic Imaging of Human Mesenchymal Stem Cells Labeled with Prussian Blue-Poly(I-lysine) Nanocomplexes." ACS nano vol. 11,9 (2017): 9022-9032. doi:10.1021/acsnano.7b03519.
Kitamura, B. Judkewitz, M. Kano, W. Denk, and M. Hausser, "Targeted patch-clamp recordings and single-cell electroporation of unla-beled neurons in vivo," Nat. methods 5, 61-67 (2008).
Kodandaramaiah, G. L. Holst, I. R. Wickersham, A. C. Singer, G. T. Franzesi, M. L. McKinnon, C. R. Forest, and E. S. Boyden, "Assembly and operation of the autopatcher for automated intracellular neural recording in vivo," Nat. protocols 11, 634-654 (2016).
Kodandaramaiah, S. B.; Boyden, E. S.; Forest, C. R.; New York Acad, S., In vivo robotics: the automation of neuroscience and other intact-system biological fields. In Conference Reports: Evolutionary Dynamics and Information Hierarchies in Biological Systems: Aspen Center for Physics Workshop and Cracking the Neural Code: Third Annual Aspen Brain Forums, Blackwell Science Publ: Oxford, 2013; vol. 1305, pp. 63-71.
Kodandaramaiah, S. B.; Franzesi, G. T.; Chow, B. Y.; Boyden, E. S.; Forest, C. R., Automated whole-cell patch-clamp electrophysiology of neurons in vivo. Nat. Methods 2012, 9 (6), 585-+.
Kodandaramaish, S. B.; Flores, F. J.; Holst, G. L.; Singer, A. C.; Han, X.; Brown, E. N.; Boyden, E. S.; Forest, C. R., Multi-neuron intracellular recording in vivo via interacting autopatching robots. eLife 2018, 7, 19.
Kozodoy, A. T. Pagkalinawan, and J. A. Harrington, "Small-bore hollow waveguides for delivery of 3-mm laser radiation," Appl. optics 35, 1077-1082 (1996).
Ku, G.; Wang, X. D.; Xie, X. Y.; Stoica, G.; Wang, L. H. V., Imaging of tumor angiogenesis in rat brains in vivo by photoacoustic tomography. Applied Optics 2005, 44 (5), 770-775.
Kumar et al., From the Bench to the Field in Low-Cost Diagnostics: Two Case Studies. Angewandte Chemie International Edition 2015, 54 (20), 5836-5853.
LeChasseur, Y.; Dufour, S.; Lavertu, G.; Bories, C.; Deschenes, M.; Vallee, R.; De Koninck, Y., A microprobe for parallel optical and electrical recordings from single neurons in vivo. Nat. Methods 2011, 8 (4), 319-U63.
Llinas, R. R., Intrinsic electrical properties of mammalian neurons and CNS function: a historical perspective. Frontiers in Cellular Neuroscience 2014, 8.
Long, L. Li, U. Knoblich, H. Zeng, and H. Peng, "3d image-guided automatic pipette positioning for single cell experiments in vivo," Sci. reports 5, 18426 (2015).

(56) References Cited

OTHER PUBLICATIONS

Long, M. A.; Jin, D. Z. Z.; Fee, M. S., Support for a synaptic chain model of neuronal sequence generation. Nature 2010, 468 (7322), 394-399.
Lu, W.; Huang, Q.; Geng, K. B.; Wen, X. X.; Zhou, M.; Guzatov, D.; Brecht, P.; Su, R.; Oraevsky, A.; Wang, L. V.; Li, C., Photoacoustic imaging of living mouse brain vasculature using hollow gold nanospheres. Biomaterials 2010, 31 (9), 2617-2626.
Lusk, Joel F., et al. "Photoacoustic Flow System for the Detection of Ovarian Circulating Tumor Cells Utilizing Copper Sulfide Nanoparticles." ACS Biomaterials Science & Engineering (2019).
Mallidi, S.; Luke, G. P.; Emelianov, S., Photoacoustic imaging in cancer detection, diagnosis, and treatment guidance. Trends in Biotechnology 2011, 29 (5), 213-221.
Margrie, A. H. Meyer, A. Caputi, H. Monyer, M. T. Hasan, A. T. Schaefer, W. Denk, and M. Brecht, "Targeted whole-cell recordings in the mammalian brain in vivo," Neuron 39, 911-918 (2003).
Markram, H.; Lubke, J.; Frotscher, M.; Roth, A.; Sakmann, B., Physiology and anatomy of synaptic connections between thick tufted pyramidal neurones in the developing rat neocortex. Journal of Physiology—London 1997, 500 (2), 409-440.
Maslov, K.; Zhang, H. F.; Hu, S.; Wang, L. V., Optical-resolution photoacoustic microscopy for in vivo imaging of single capillaries. Opt. Lett. 2008, 33 (9), 929-931.
Matsuura, T. Abel, and J. A. Harrington, "Optical properties of smallbore hollow glass waveguides," Appl. optics 34, 6842-6847 (1995).
Matsuura, T. Abel, J. Hirsch, and J. Harrington, "Small-bore hollow waveguide for delivery of near singlemode ir laser radiation," Electron. Lett. 30, 1688-1690 (1994).
Miranda et al., "Side-viewing Photoacoustic Capillary Endoscope," 2018, Optics Letters, 1-5.
Miranda, C.; Barkley, J.; Smith, B. S., Intrauterine photoacoustic and ultrasound imaging probe. J. Biomed. Opt. 2018, 23 (4), 9.
Miranda, Christopher, et al. "Photoacoustic micropipette." Applied Physics Letters 113.26 (2018): 264103.
Neher, E.; Sakmann, B., single-channel currents recorded from membrane of denervated frog muscle-fibers. Nature 1976, 260 (5554), 799-802.
Nichols, J.; Bjorklund, G. R.; Newbern, J.; Anderson, T., Parvalbumin fast-spiking interneurons are selectively altered by paediatric traumatic brain injury. Journal of Physiology—London 2018, 596(7), 1277-1293.
Nichols, J.; Perez, R.; Wu, C.; Adelson, P. D.; Anderson, T., Traumatic Brain Injury Induces Rapid Enhancement of Cortical Excitability in Juvenile Rats. Cns Neuroscience & Therapeutics 2015, 21 (2), 193-203.
Olsen, S. R.; Wilson, R. I., Cracking neural circuits in a tiny brain: new approaches for understanding the neural circuitry of *Drosophila*. Trends in Neurosciences 2008, 31 (10), 512-520.
Ovsepian, Saak V., et al. "Pushing the boundaries of neuroimaging with optoacoustics." Neuron 96.5 (2017): 966-988.
Papadopoulos, O. Simandoux, S. Farahi, J. Pierre Huignard, E. Bossy, D. Psaltis, and C. Moser, "Optical-resolution photoacoustic microscopy by use of a multimode fiber," Appl. Phys. Lett. 102, 211106 (2013).
Papadopoulos, S. Farahi, C. Moser, and D. Psaltis, "Highresolution, lensless endoscope based on digital scanning through a multimode optical fiber," Biomed. optics express 4, 260-270 (2013).
Patil, Ujwal, et al. "In vitro/in vivo toxicity evaluation and quantification of iron oxide nanoparticles." International journal of molecular sciences 16.10 (2015): 24417-24450.
Pisanello, F.; Sileo, L.; Oldenburg, I. A.; Pisanello, M.; Martiradonna, L.; Assad, J. A.; Sabatini, B.L.; De Vittorio, M., Multipoint-Emitting Optical Fibers for Spatially Addressable In Vivo Optogenetics. Neuron 2014, 82 (6), 1245-1254.
Richter, D. W.; Pierrefiche, O.; Lalley, P. M.; Polder, H. R., Voltage-clamp analysis of neurons within deep layers of the brain. J. Neurosci. Methods 1996, 67 (2), 121-131.
Rose, G. J.; Alluri, R. K.; Vasquez-Opazo, G. A.; Odom, S. E.; Graham, J. A.; Leary, C. J., Combining pharmacology and whole-cell patch recording from CNS neurons, in vivo. J. Neurosci. Methods 2013, 213 (1), 99-104.
Saiki, T.; Matsuda, K., Near-field optical fiber probe optimized for illumination-collection hybrid mode operation. Applied Physics Letters 1999, 74 (19), 2773-2775.
Schneider, D. M.; Nelson, A.; Mooney, R., A synaptic and circuit basis for corollary discharge in the auditory cortex. Nature 2014, 513 (7517), 189-+.
Sethuraman, S. R. Aglyamov, J. H. Amirian, R. W. Smalling, and S. Y. Emelianov, "Intravascular photoacoustic imaging using an ivus imaging catheter," IEEE transactions on ultrasonics, ferroelectrics, frequency control 54 (2007).
Shi, K. Ito, L. Ma, T. Yoshida, Y. Matsuura, and M. Miyagi, "Fabrication of a polymer-coated silver hollow optical fiber with high performance," Appl. optics 45, 6736-6740 (2006).
Shung, J. Cannata, and Q. Zhou, "Piezoelectric materials for high frequency medical imaging applications: A review," J. Electroceramics 19, 141-147 (2007).
Simandoux, N. Stasio, J. Gateau, J.-P. Huignard, C. Moser, D. Psaltis, and E. Bossy, "Optical-resolution photoacoustic imaging through thick tissue with a thin capillary as a dual optical-in acousticout waveguide," Appl. Phys. Lett. 106, 094102 (2015).
Smetters, D.; Majewska, A.; Yuste, R., Detecting action potentials in neuronal populations with calcium imaging. Methods—a Companion to Methods in Enzymology 1999, 18 (2), 215-221.
Smith, A Shah, Yong-Kyun Lee, B O'Brien, D Kullman, A Sridharan, J Muthuswamy, J B Christen "Optogenetic Neurostimulation of the Auricular Vagus using Flexible OLED Display Technology to Treat Chronic Inflammatory Disease and Mental Health Disorders" Electronics Letters, DOI: 10.1049/e1.2015.3450, 2016.
So, P. T. C.; Dong, C. Y.; Masters, B. R.; Berland, K. M., Two-photon excitation fluorescence microscopy. Annual Review of Biomedical Engineering 2000, 2, 399-429.
Stasio, A. Shibukawa, I. N. Papadopoulos, S. Farahi, O. Simandoux, J.-P. Huignard, E. Bossy, C. Moser, and D. Psaltis, "Towards new applications using capillary waveguides," Biomed. optics express 6, 4619-4631 (2015).
Stern, E. A.; Kalman, Z.; Lewis, A.; Lieberman, K., simple method for focusing x-rays using tapered capillaries. Applied Optics 1988, 27 (24), 5135-5139.
Stosiek, C.; Garaschuk, O.; Holthoff, K.; Konnerth, A., In vivo two-photon calcium imaging of neuronal networks. Proc. Natl. Acad. Sci. U. S. A. 2003, 100 (12), 7319-7324.
Strohm, E. M.; Moore, M. J.; Kolios, M. C., Single Cell Photoacoustic Microscopy: A Review. Ieee Journal of Selected Topics in Quantum Electronics 2016, 22 (3).
Stuart, G. J.; Dodt, H. U.; Sakmann, B., patch-clamp recordings from the soma and dendrites of neurons in brain-slices using infrared video microscopy. Pflugers Arch. 1993, 423 (5-6), 511-518.
Suk, I. van Welie, S. B. Kodandaramaiah, B. Allen, C. R. Forest, and E. S. Boyden, "Closed-loop real-time imaging enables fully automated cell-targeted patch-clamp neural recording in vivo," Neuron. 95, 1037-1047 (2017).
Svoboda, K.; Yasuda, R., Principles of two-photon excitation microscopy and its applications to neuroscience. Neuron 2006, 50 (6), 823-839.
Timofeev, I.; Grenier, F.; Steriade, M., Disfacilitation and active inhibition in the neocortex during the natural sleep-wake cycle: An intracellular study. Proc. Natl. Acad. Sci. U. S. A. 2001, 98 (4), 1924-1929.
Vasilyev, D.; Merrill, T.; Iwanow, A.; Dunlop, J.; Bowlby, M., A novel method for patch-clamp automation. Pflugers Arch. 2006, 452 (2), 240-247.
Veerman, J. A.; Otter, A. M.; Kuipers, L.; van Hulst, N. F., High definition aperture probes for nearfield optical microscopy fabricated by focused ion beam milling. Applied Physics Letters 1998, 72 (24), 3115-3117.
Wang and S. Hu, "Photoacoustic tomography: in vivo imaging from organelles to organs," Science 335, 1458-1462 (2012).

(56) References Cited

OTHER PUBLICATIONS

Wang, A. Karpiouk, D. Yeager, J. Amirian, S. Litovsky, R. Smalling, and S. Emelianov, "Intravascular photoacoustic imaging of lipid in atherosclerotic plaques in the presence of luminal blood," Opt. letters 37, 1244-1246 (2012).

Wang, C.-C.; Hennek, J. W.; Ainla, A.; Kumar, A. A.; Lan, W.-J.; Im, J.; Smith, B. S.; Zhao, M.; Whitesides, G. M., A Paper-Based "Pop-up" Electrochemical Device for Analysis of Beta-Hydroxybutyrate. Analytical Chemistry 2016, 88 (12), 6326-6333.

Wang, J. L. Su, A. B. Karpiouk, K. V. Sokolov, R. W. Smalling, and S. Y. Emelianov, "Intravascular photoacoustic imaging," IEEE J. selected topics Quantum Electron. 16, 588-599 (2010).

Wang, L. V., Multiscale photoacoustic microscopy and computed tomography. Nature Photonics 2009, 3 (9), 503-509.

Wang, T. Ma, M. N. Slipchenko, S. Liang, J. Hui, K. K. Shung, S. Roy, M. Sturek, Q. Zhou, Z. Chen, and J.-X. Cheng, "High-speed intravascular photoacoustic imaging of lipid-laden atherosclerotic plaque enabled by a 2-khz barium nitrite raman laser," Sci. reports 4, 6889 (2014).

Wang, X. D.; Pang, Y. J.; Ku, G.; Xie, X. Y.; Stoica, G.; Wang, L. H. V., Noninvasive laser-induced photoacoustic tomography for structural and functional in vivo imaging of the brain. Nat. Biotechnol. 2003, 21 (7), 803-806.

Wang, X. D.; Xie, X. Y.; Ku, G. N.; Wang, L. H. V., Noninvasive imaging of hemoglobin concentration and oxygenation in the rat brain using high-resolution photoacoustic tomography. J. Biomed. Opt. 2006, 11 (2).

Weber, Judith, Paul C. Beard, and Sarah E. Bohndiek. "Contrast agents for molecular photoacoustic imaging." Nature methods 13.8 (2016): 639.

Wong, Terence TW, et al. "Fast label-free multilayered histology-like imaging of human breast cancer by photoacoustic microscopy." Science advances 3.5 (2017): e1602168.

Wu, I. Kolb, B. M. Callahan, Z. Su, W. Stoy, S. B. Kodandaramaiah, R. Neve, H. Zeng, E. S. Boyden, C. R. Forest, and A. A. Chubykin, "Integration of autopatching with automated pipette and cell detection in vitro," J. neurophysiology 116, 1564-1578 (2016).

Xu, Minghua, and Lihong V. Wang. "Photoacoustic imaging in biomedicine." Review of scientific instruments 77.4 (2006): 041101.

Yajuan, X.; Xin, L.; Zhiyuan, L., A comparison of the performance and application differences between manual and automated patch-clamp techniques. Curr Chem Genomics 2012, 6, 87-92.

Yang, C. Favazza, J. Yao, R. Chen, Q. Zhou, K. K. Shung, and L. V. Wang, "Three-dimensional photoacoustic endoscopic imaging of the rabbit esophagus," PloS one 10, e0120269 (2015).

Yang, C. Favazza, R. Chen, J. Yao, X. Cai, K. Maslov, Q. Zhou, K. K. Shung, and L. V. Wang, "Simultaneous functional photoacoustic and ultrasonic endoscopy of internal organs in vivo," Nat. medicine 18, 1297-1302 (2012).

Yang, C. Favazza, R. Chen, K. Maslov, X. Cai, Q. Zhou, K. K. Shung, and L. V. Wang, "Volumetric photoacoustic endoscopy of upper gastrointestinal tract: ultrasonic transducer technology development," in Proc. SPIE, , vol. 7899 (2011), pp. 78990D1-78990D6.

Yang, K. Maslov, H.-C. Yang, Q. Zhou, K. K. Shung, and L. V. Wang, "Photoacoustic endoscopy," Opt. letters 34, 1591-1593 (2009).

Yang, R.; Lai, K. W. C.; Xi, N.; Yang, J., Development of automated patch clamp system for electrophysiology. In 2013 IEEE International Conference on Robotics and Biomimetics, ROBIO 2013, 2013; p. 2185.

Yang, R.; Tam, C. H.; Cheung, K. L.; Wong, K. C.; Xi, N.; Yang, J.; Lai, W. C. K., Cell Segmentation and Pipette Identification for Automated Patch Clamp Recording. Robotics and Biomimetics 2014, 1 (20), 1-12.

Yao, K. Maslov, K. K. Shung, Q. Zhou, and L. V. Wang, "In vivo label-free photoacoustic microscopy of cell nuclei by excitation of dna and rna," Opt. letters 35, 4139-4141 (2010).

Yizhar, O.; Fenno, L. E.; Davidson, T. J.; Mogri, M.; Deisseroth, K., Optogenetics in Neural Systems. Neuron 2011, 71 (1), 9-34.

Zhang and P. C. Beard, "A miniature all-optical photoacoustic imaging probe," in Proc. SPIE, , vol. 7899 (2011), p. 78991F.

Zhang, C.; Maslov, K.; Wang, L. H. V., Subwavelength-resolution label-free photoacoustic microscopy of optical absorption in vivo. Opt. Lett. 2010, 35 (19), 3195-3197.

Zhang, H. F.; Maslov, K.; Stoica, G.; Wang, L. H. V., Functional photoacoustic microscopy for high-resolution and noninvasive in vivo imaging. Nat. Biotechnol. 2006, 24 (7), 848-851.

Zhang, J. Y.; Laiwalla, F.; Kim, J. A.; Urabe, H.; Van Wagenen, R.; Song, Y. K.; Connors, B. W.; Zhang, F.; Deisseroth, K.; Nurmikko, A. V., Integrated device for optical stimulation and spatiotemporal electrical recording of neural activity in light-sensitized brain tissue. Journal of Neural Engineering 2009, 6 (5).

Zharov, V. P.; Galanzha, E. I.; Shashkov, E. V.; Khlebtsov, N. G.; Tuchin, V. V., In vivo photoacoustic flow cytometry for monitoring of circulating single cancer cells and contrast agents. Opt. Lett. 2006, 31 (24), 3623-3625.

Zharov, V. P.; Galanzha, E. I.; Shashkov, E. V.; Kim, J. W.; Khlebtsov, N. G.; Tuchin, V. V., Photoacoustic flow cytometry: principle and application for real-time detection of circulating single nanoparticles, pathogens, and contrast dyes in vivo. J. Biomed. Opt. 2007, 12 (5).

Kuck, N., et al. "Visible electroluminescent subwavelength point source of light." Applied physics letters 61.2 (1992): 139-141.

Thor Labs "Achromatic Pairs" 2011 (Year: 2011) (3 pages).

Freudenrich, C. How Fiber Optics Work. Mar. 6, 2001, HowStuffWorks. com, pp. 1-9 (Year: 2001).

\* cited by examiner

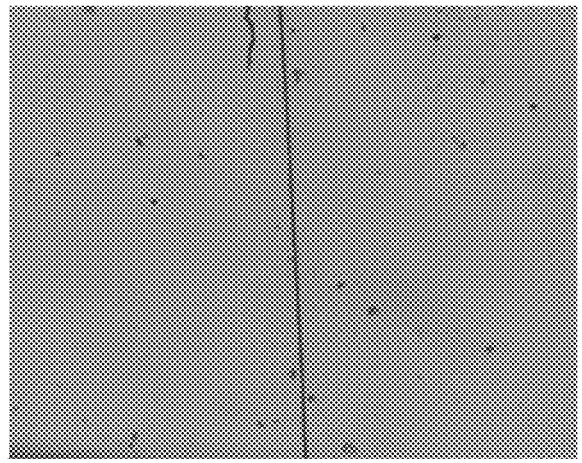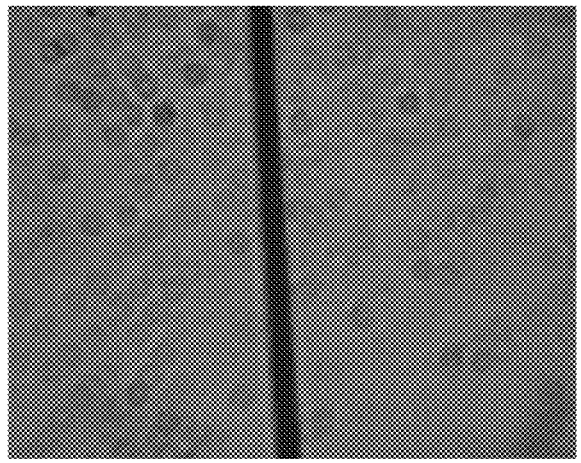
FIG. 7A        FIG. 7B
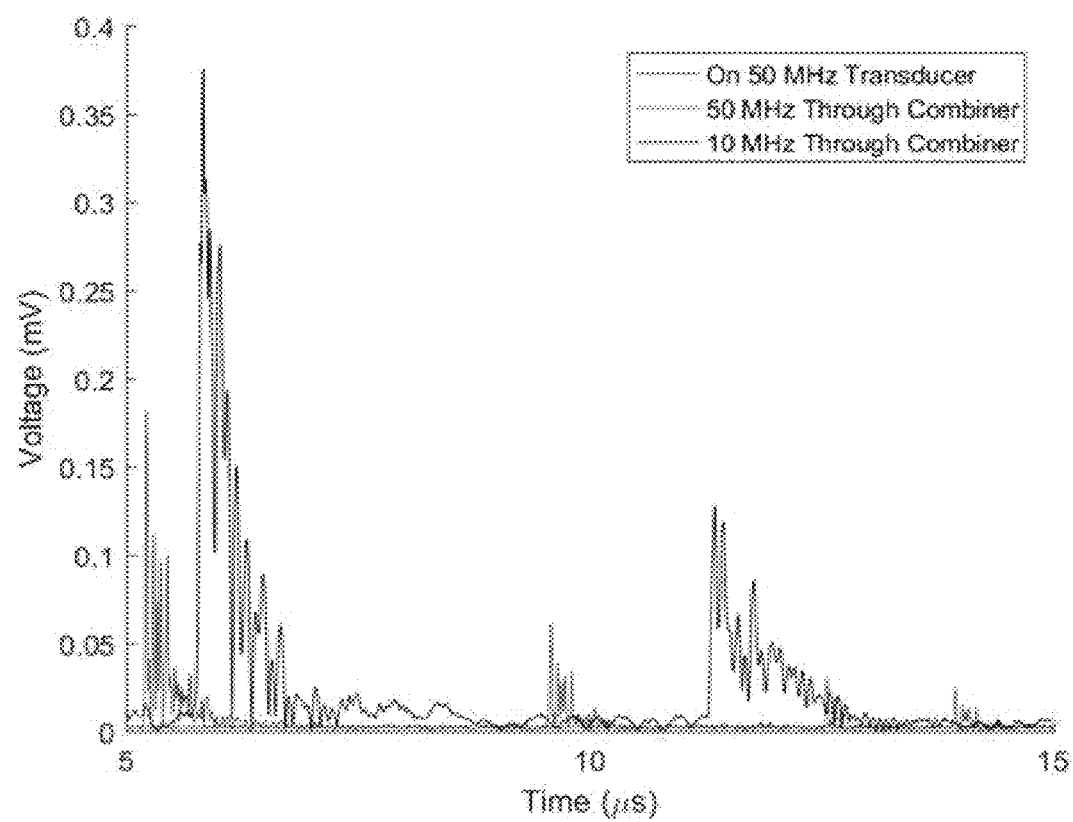
FIG. 8

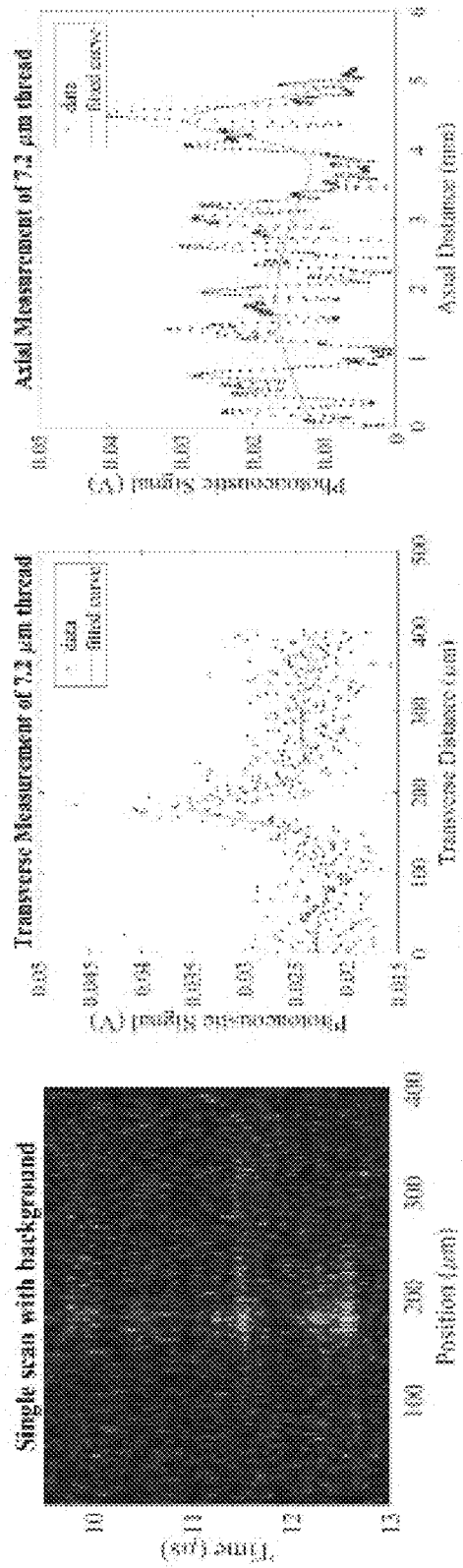
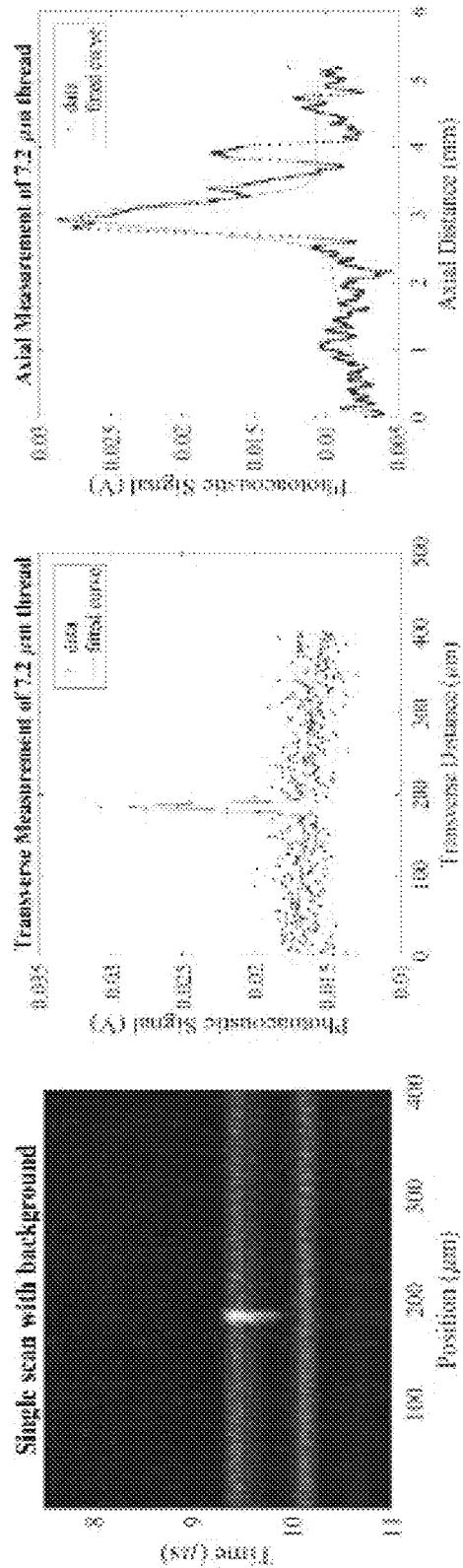
FIG. 10A  FIG. 10B  FIG. 10C  FIG. 10D  FIG. 10E  FIG. 10F

PHOTOACOUSTIC AND OPTICAL MICROSCOPY COMBINER AND METHOD OF GENERATING A PHOTOACOUSTIC IMAGE OF A SAMPLE

CROSS-REFERENCE TO RELATED APPLICATIONS

This application is a non-provisional of and claims the benefit of U.S. Provisional Patent Application No. 62/839,604, filed on Apr. 26, 2019, the contents of which are incorporated herein by reference.

BACKGROUND

The photoacoustic effect is the phenomenon of an acoustic wave being generated as a consequence of electromagnetic wave absorption. When non-ionizing laser pulses are delivered, some energy gets converted to heat, causing the thermoelastic expansion, and then the generation of an ultrasonic wave from the rapid pressure differential. This effect relies on the differential thermoelastic expansion of the tissue, allowing the ability to examine the tissue in what is known as photoacoustic imaging.

Photoacoustic imaging is an imaging modality which derives contrast from the differences in optical absorption of the sample being analyzed, which may result from cellular structure, chemical structure, biologicals and the like, combining the high contrast of optical imaging with the resolution and improved depth of ultrasound. This technique has promise in its ability to differentiate characteristics of living tissue as physiological changes may affect the optical properties of a structure. Some endogenous molecules providing contrast may include DNA, RNA, hemoglobin, water, and lipids. Further contrast is possible through various means, such as dyes or receptor-specific absorbers, with popular examples being fluorescent proteins and nanoparticles.

A typical photoacoustic imaging system is comprised of a pulse-energy source and an acoustic detector—multiple variations of this system exist. This has important and widespread application in areas ranging from cancer detection to brain mapping. An example of photoacoustic stem cell imaging would include the use of photoacoustic contrast agents, such as gold nanocages, to track stem cell homing to tumors, gold nanorods for human mesenchymal stem cells, or Prussian blue nanoparticles. In the case of brain mapping, contrast-free photoacoustic imaging is able to capture high-resolution images and capture data for blood oxygenation, total hemoglobin, blood volume, and more in real-time, as opposed to the minutes required for MRI technologies.

For high resolution photoacoustic imaging, typically photoacoustic microscopy (PAM) is employed. This technique involves the concentration of light at small, specific spatial points in order to induce the photoacoustic effect. One method of light concentration is through optical waveguides.

SUMMARY

The technique of photoacoustic microscopy and brightfield imaging may be combined. Photoacoustic microscopy is improved for use with, for example, whole-cell patch-clamping, an electrophysiology technique used to study a substantial part of the neurons—useful for shedding light on the passive and active biophysical properties of excitable cells, especially of the effect of specific manipulations on neuronal function.

This disclosure describes a system for allowing for simultaneous optical and photoacoustic imaging. A polylactic acid (PLA) model has been designed and constructed which allows for both optical zoom (e.g., 40×) and photoacoustic microscopy of samples on 12 mm glass slides. Raster scanning of black tape and a carbon fiber thread with a 7.2 micrometer diameter has been shown to successfully integrate photoacoustic and optical microscopy.

A novel imaging platform has been developed, where photoacoustics and optical microscopy are combined to enable real-time imaging of a 2D sample. The combiner is capable of integration with many different commercially available microscopes (at a variety of magnifications) and can be adjusted to integrate with a wide variety of commercially available or custom made transducers. Additionally, variations of the "handle" allow for adaptability with various hardware configurations (e.g., inserted into the railing of a micromanipulator, integrated with an electrophysiology setup, secured by a V-clamp, etc.). This tool provides a new platform for photoacoustic microscopy studies, enabling real-time photoacoustic microscopy simultaneously with optical microscopy at high resolution.

Algorithms developed reconstruct the resulting ultrasound data to produce a real-time image of the sample. The effective combination of optical and photoacoustic imaging may be a powerful tool across a wide variety of fields, including, but not limited to: biomedical (tissue) engineering, micro/nano-scale systems, material science (e.g., surface treatments and topographies), nanoscience, electrophysiology, near field imaging, physics, and molecular sciences.

In one construction, a photoacoustic and optical microscopy combiner is provided. The combiner is configured to support a transducer defining an axis. The combiner includes a body including a base and an opening extending through the base, and a glass member at least partially positioned within the opening. The glass member includes a surface positioned at an angle relative to the base and the axis of the transducer. A sample slide is supported on the body and at least partially over the opening. The sample slide is positioned such that a sample on the sample slide is configured to receive light from a laser and redirect the light to an ultrasound transducer to generate a real-time image of a sample.

In another construction, a photoacoustic and optical microscopy combiner is provided. The combiner is configured to support a transducer defining an axis. The combiner includes a base and a reservoir, an angled surface positioned within the body, the angled surface oriented at a 45-degree angle relative to the base and the axis of the transducer, and a glass member positionable within the body and at least partially supported by the angled surface and at least partially over the opening, the glass member including a face that is oriented parallel to angled surface. A sample slide is supported on the body, and is positioned such that a sample on the sample slide is configured to receive light from a laser and redirect the light to an ultrasound transducer to generate a real-time image of a sample.

In another construction, a method of generating a photoacoustic image of a sample is provided. The method includes generating a sub-diffraction spot size by applying a pulsed wave laser light through an optical fiber, delivering the pulsed wave laser light toward the sample, detecting, with a transducer, acoustic waves due to thermoelastic expansion of the sample, and generating a super-resolution two-dimensional image from signals sent from the transducer to a processor.

Other aspects of the invention will become apparent by consideration of the detailed description and accompanying drawings.

BRIEF DESCRIPTION OF THE DRAWINGS

FIG. 7A illustrates a detection area on 4× magnification of a 7.2 μm carbon fiber thread using the combiner of FIG. 2A.

FIG. 7B illustrates a detection area on 40× magnification of a 7.2 μm carbon fiber thread using the combiner of FIG. 4A.

FIG. 8 is shows the raw data comparing the output of the GPGP with 50 MHz transducer, GSW with 50 MHz transducer, and GSW with a 10 MHz transducer.

FIG. 10A illustrates a photoacoustic image reconstruction of a 7.2 μm carbon fiber thread using the combiner of FIG. 2A.

FIG. 10B illustrates a photoacoustic image reconstruction of a 7.2 μm carbon fiber thread using the combiner of FIG. 4A.

FIG. 10C illustrates transverse measurements using the combiner of FIG. 2A.

FIG. 10D illustrates transverse measurements using the combiner of FIG. 4A.

FIG. 10E illustrates vertical measurements using the combiner of FIG. 2A.

FIG. 10F illustrates vertical measurements using the combiner of FIG. 4A.

DETAILED DESCRIPTION

Before any constructions of the invention are explained in detail, it is to be understood that the invention is not limited in its application to the details of construction and the arrangement of components set forth in the following description or illustrated in the following drawings. The invention is capable of other constructions and of being practiced or of being carried out in various ways.

Figure 2A:
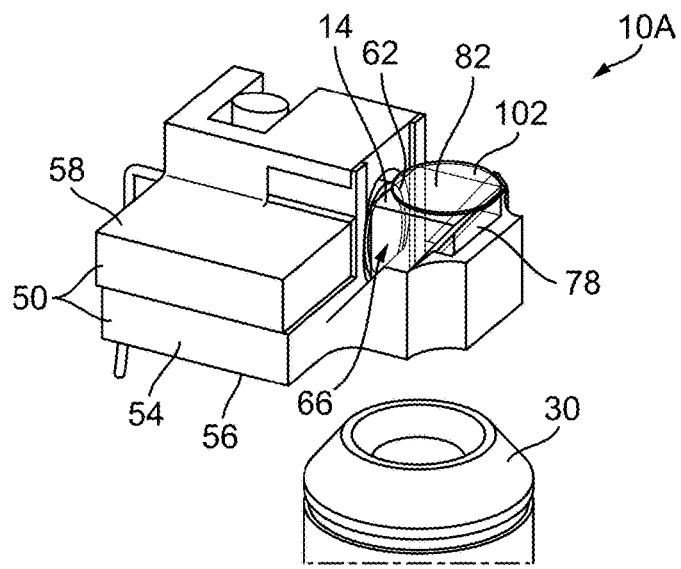
FIG. 2A illustrates a combiner according to a construction.

As discussed in greater detail below, this disclosure provides for various constructions of a combiner 10 to allow redirection of ultrasound with minimal optical aberration for dual optical and photoacoustic microscopy. In the constructions of FIGS. 2A-3, the combiners 10A include a glass-prism glass-prism (GPGP) or dual prism configuration. In the constructions of FIGS. 4A-6, the combiners 10B include a glass slide and water (GSW) configuration. Each of the combiners 10A, 10B support a transducer 14 (e.g., ultrasound transducer) or a piezoelectric crystal (e.g., one or an array of piezoelectric crystals). All of the combiners 10A, 10B are used to transmit a signal.

Figure 1:
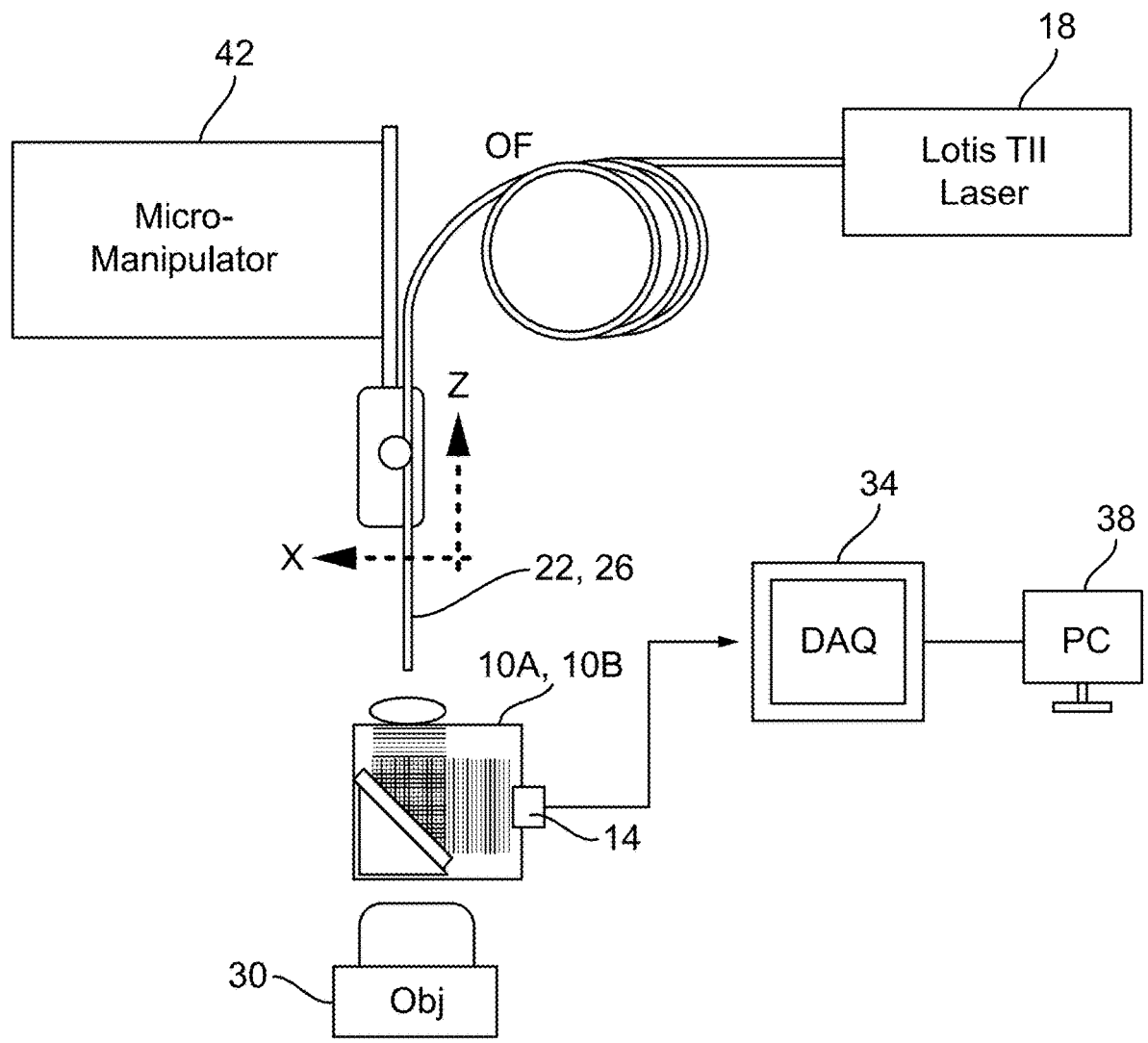
FIG. 1 is an exemplary schematic of a laser-combiner set-up.

As shown in FIG. 1, the combiners 10A, 10B of FIGS. 2A-6 are used in combination with a laser 18, a fiber optic 22 or pulled fiber or micropipette 26, an objective 30 of an inverted microscope (not shown), a data acquisition (DAQ) system 34, a processor 38 (e.g., a process), and a micromanipulator 42. The respective combiner 10A, 10B is kept in place (e.g., suspended) over the objective 30 of the inverted microscope with a V-clamp (not shown), which also serves as a relative leveler, attached to a three-axis stage (not shown). The laser 18 may be any pulsed laser. In some constructions, the laser 18 may be a pulsed tunable laser. The laser 18 may emit a wavelength of 200 nm to 2500 nm, in other constructions. In one construction, the laser 18 is a tunable LS-2134-Lt40 Nd:YAG/Ti:Sapphire nanosecond pulsed laser (e.g., Symphotic TII, Co) that emits a 460 nm wavelength for photoacoustic excitation. The emitted light from the laser 18 may have a pulse repetition rate of 1 Hz to 500 MHz, in other constructions. The emitted light from the laser 18 may have a pulse repetition rate of 10 Hz and a full width at half maximum (FWHM) of 12-15 ns. The laser 18 emits light to the fiber optic 22, which transmits the light to the combiner 10A, 10B. As shown, the fiber optic 22 has a tip that is positioned above (e.g., suspended over) and adjacent to the cover positioned atop the combiner 10A, 10B. In other constructions, the fiber optic 22 may be replaced with a pulled fiber 26, discussed in greater detail below. In other constructions, light is first attenuated using a series of neutral density filters and coupled to a single fiber-optic. Signals generated by the combiner 10A, 10B are sent from the transducer 14 to the DAQ system 34 for processing by the processor 38. Since the combiners 10A, 10B are positioned over the objective 30 of the inverted microscope, this allows optical imaging underneath the sample slide and allows the acoustic signal to be redirected into an adjacent ultrasound transducer 14.

Figure 2B:
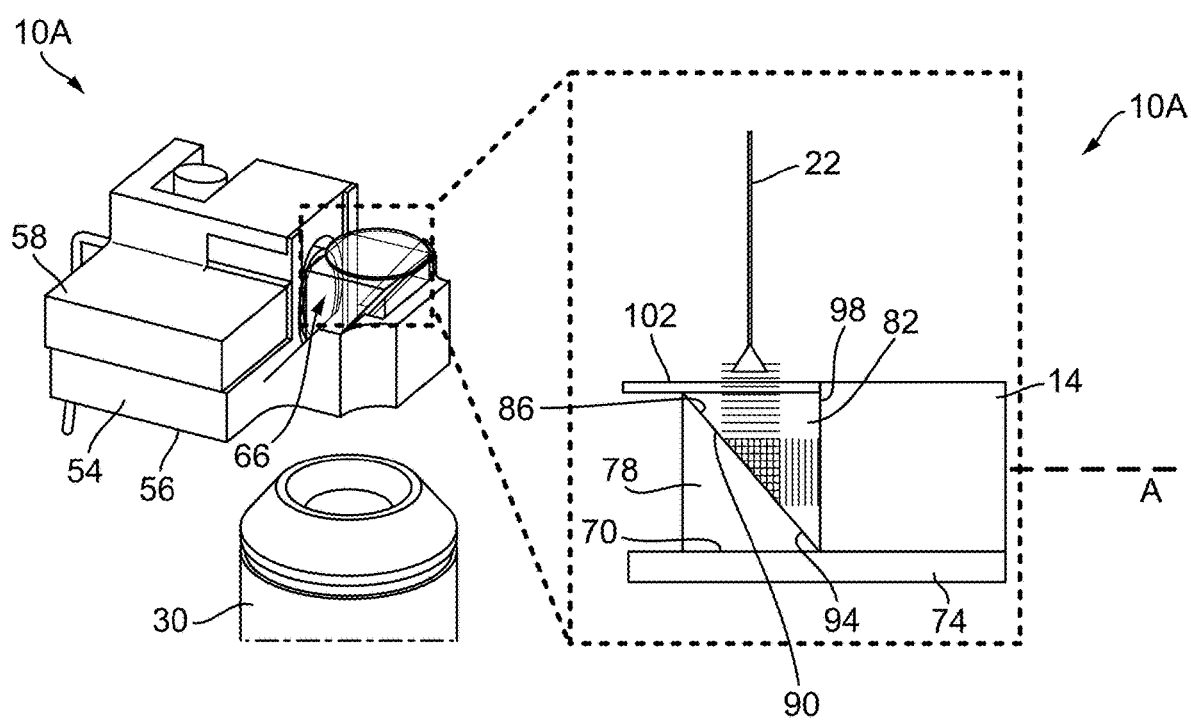
FIG. 2B illustrates a schematic representation of the signal pathway within the combiner shown in FIG. 2A.
Figure 3:
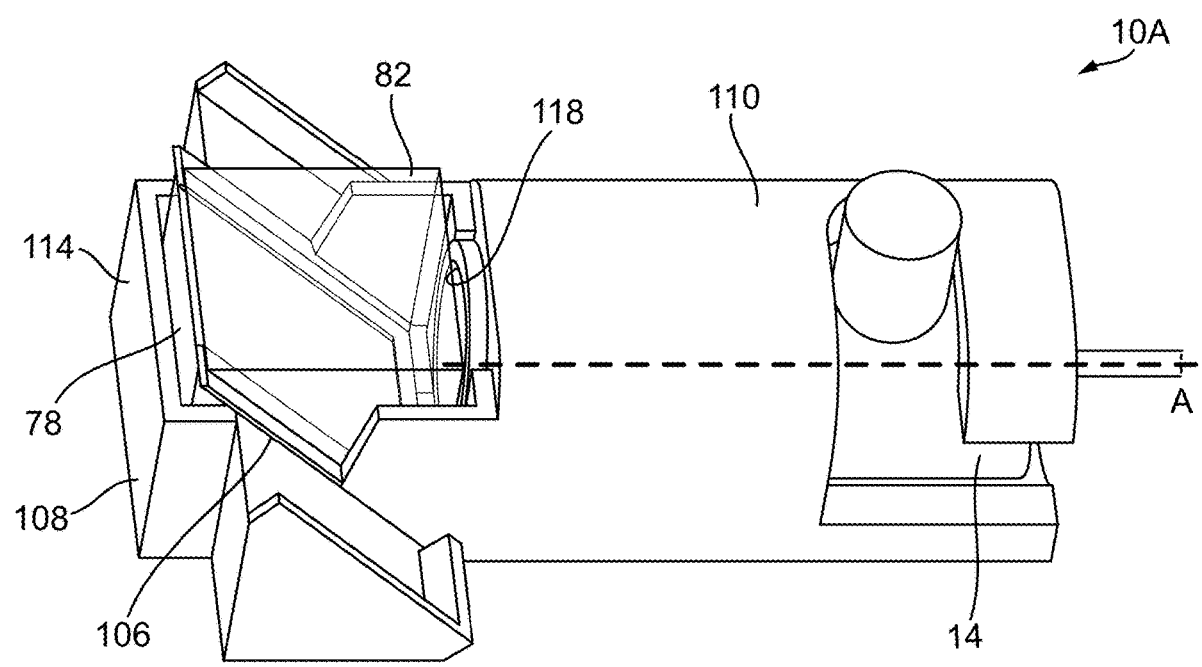
FIG. 3 illustrates a rendering of a combiner according to another construction.

FIGS. 2A and 2B illustrate the GPGP or a dual prism configured combiner 10A. As shown, the combiner 10 includes a body 50 having a first body portion 54 having a base 56 and a second body portion 58. The transducer 14 is positioned in an aperture or bore 62 in the second body portion 58 and extends between the first and second body portions 54, 58. The first body portion 54 extends beyond a perimeter of the second body portion 58. As shown, the first body portion 54 includes a gap or space 66 that is positioned adjacent to the aperture 62 that receives the transducer 14. The gap 66 creates an opening 70 in the base 56 of the first body portion 54. The body 50 is positionable on a glass member or slide 74 (e.g., transparent support member), which closes the opening 70. The gap 66 receives first and second right-angle glass prisms 78, 82 (e.g., right-angle 10 cm glass prisms manufactured by Thorlabs, Inc). While the prisms are glass in the illustrated construction, in other constructions, the prisms may be constructed from any material that is optically clear. Each of the right-angle prisms 78, 82 includes a diagonal face 86, 90. When properly positioned, the first and second right-angle prisms 78, 82 form a cube with the diagonal faces 86, 90 thereof facing (e.g., mating or being positioned adjacent) one another and creating a gap therebetween. A layer of gel 94 (e.g., a first gel layer) of silicone-based organic polymer, such as polydimethylsiloxane (PDMS) (e.g., manufactured by Sigma-Aldrich) or acoustic gel, is positioned within the gap between the two prisms 78, 82 to create a consistent refractive index for optical transmission, and inconsistent acoustic impedance for ultrasound redirection. In particular, the PDMS is positioned between the diagonal faces 86, 90 of the two right-angle prisms 78, 82. The PDMS may be applied atop the diagonal faces 86, 90 of the prisms 78, 82 using a 12 mL syringe and 18-gauge needle (BD). While PDMS is used in the illustrated construction, the gel may be any other suitable gel, oil or liquid that has a refractive index similar to the material (e.g., glass in this construction) of the prism to allow visualization of the sample with the objective lens 30, and must also have an acoustic impedance that is different from the material of the prism to re-direct sound. The resulting cube is positionable within the gap 66 in the first body 54 portion adjacent the transducer 14. As shown, the resulting cube sits on a surface of the glass member 74. As shown, the diagonal faces 86, 90 are positioned at a 45-degree angle relative to a plane form by the base 56 and an axis A of the transducer 14. The diagonal faces 86, 90 may be positioned at other angles, for example, 0 degrees to 180 degrees. Another layer of gel 98 (e.g., a second gel layer) of silicone-based organic polymer, such as PDMS, may be applied at the interface between one of the first and second prisms 78, 82 and the transducer 14. In the illustrated construction, the transducer 14 is a 50 MHz transducer 14. In other constructions, the first and second gel layers 94, 98 may be acoustic gel, which may provide a reduced signal to noise ratio. The first and second gel layers 94, 98 may be reapplied between uses because the material may leak due to its low-viscosity. In yet other constructions, a spacer 106 (FIG. 3) may be used in addition to or in lieu of the first and second gel layers 94, 98. The spacer 106 may be, for example, a glass spacer having a thickness of 200 mm. The spacer 106 maintains a fixed distance between the two right angle prisms 78, 82. The spacer only contacts both right angle prisms 78, 72 along the perimeters thereof so that it does not obstruct the view from the objective lens 30 or affect the sound being redirected. A cover or sample slide 102 containing the sample to be analyzed may be positioned over the two right-angle prisms 78, 82 during use.

In the construction of FIG. 3, the body of the combiner 10A has a different configuration; only the differences are discussed herein. In contrast to the construction of FIGS. 2A and 2B, which has first and second body portions 54, 58, the construction of FIG. 3 has a single, integrally formed (e.g., formed in one-piece) body 108. As shown, the body 108 of the combiner 10A of FIG. 3 has a first, elongated portion 110 that receives the transducer 14 and a second portion 114 integrally formed with the elongated portion 110. The second portion 114 defines an aperture or bore 118 that receives the first and second dual prisms 78, 82.

Figure 4A:
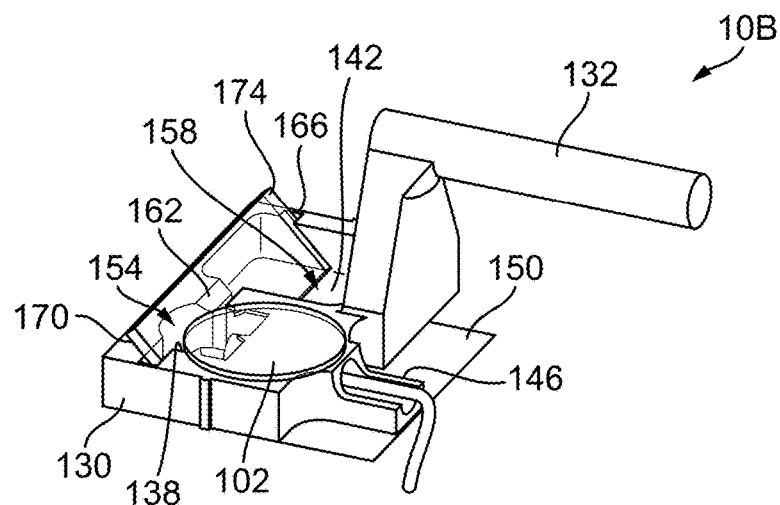
FIG. 4A illustrates a combiner according to another construction.
Figure 4B:
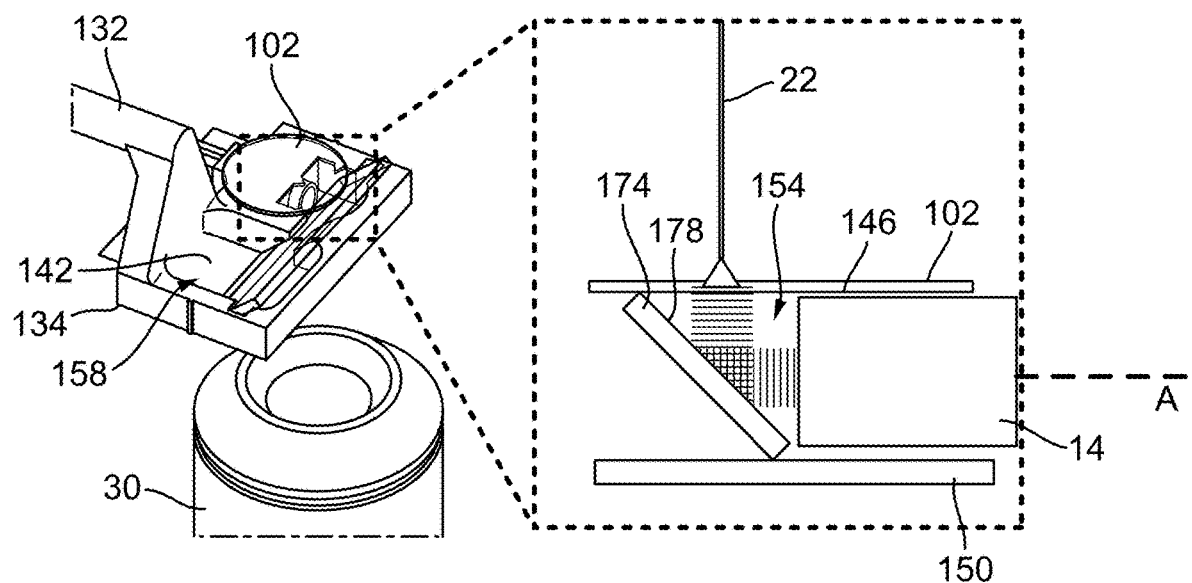
FIG. 4B illustrates a schematic representation of the signal pathway within the combiner shown in FIG. 4A.

FIGS. 4A and 4B illustrate the GSW combiner configuration according to one construction. The GSW combiner 10B includes a body 130 with handle 132, a base 134, an opening 138, and a recess 142 in fluid communication with the opening 138. The body further includes an aperture or bore 146 that receives and secures the transducer 14 and is positioned adjacent the opening 138. A first glass member 150 (e.g., transparent support member) is coupled to the base 134 by optical glue (e.g., manufactured by Norland Products, Inc.), for example, or any other suitable adhesive. The optical glue secures and ensures tight bonding and leak resistance between the first glass member 150 and the body 130. Accordingly, the opening 138 and the recess 142 define respective first and second reservoirs 154, 158. A wall 162 is positioned between and at least partially defines each of the opening 138 and recess 142. The wall 162 is an angled wall, and each of the opening 138 and the recess 142 may each have a respective angled wall 166, 170. A surface of the angled walls 162, 166, 170 defines a plane that is positioned at a 45-degree angle relative to the base 134 of the body 130 and the axis A of the transducer 14. A second glass member 174 is positionable or coupleable within the opening 138 and may be at least partially supported by the first glass member 150. The second glass member 174 has a face 178 that is oriented at a 45-degree angle relative to the base and the axis A of the transducer 14. As shown, the second glass member 174 is positionable against the walls 162, 166, 170 such that the third glass member 174 is positioned at the 45-degree angle relative to the base 134 of the body 130 and the axis A of the transducer 14. In the illustrated construction, the second glass member substantially rectangular. In other constructions, the second glass member 174 may have other configurations (e.g., a right-angle glass prism) having a diagonal face that is positionable at the 45-degree angle relative to the base 130 and the axis A of the transducer 14. A fluid may be introduced into the first and second reservoirs 154, 158 to submerge the first and second glass members 150, 174. The fluid may be water or any other fluid that would not interfere with the optical or photoacoustic imaging. The water may be selected from the group consisting of deionized water, distilled water, filtered water, reverse osmosis water, or any combination of these. In some constructions, the water may be deionized (DI) water. The DI water is applied using a 12 mL syringe and 18-gauge needle (BD) into the first and second reservoirs 154, 158. Surface tension eliminates any air bubbles on the first and second glass members 150, 174. A cover 102 containing the sample to be analyzed is positionable over the opening 138 and reservoir 154, as shown, during use. While the members 150, 174 are glass in the illustrated construction, in other constructions, the members 150, 174 may be constructed from any material that is optically clear.

Figure 5:
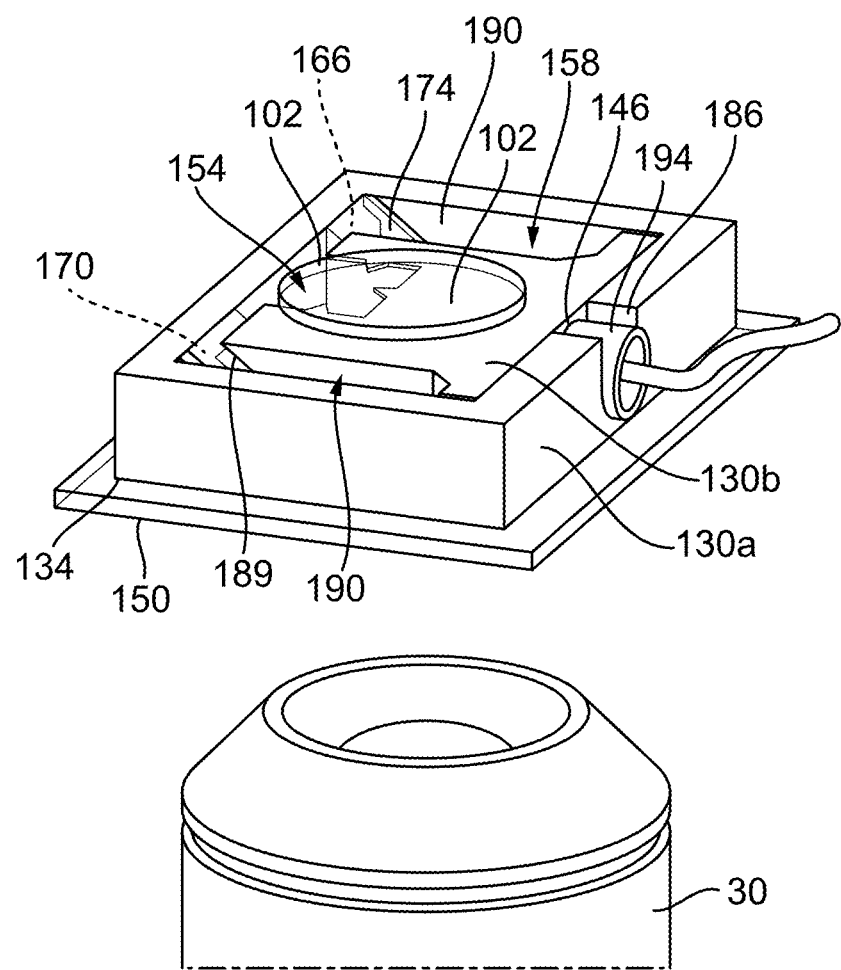
FIG. 5 illustrates a rendering of a combiner according to another construction.

Another construction of a GSW combiner 10B is shown in FIG. 5. Only the differences between the construction of FIGS. 4A and 4B and the construction of FIG. 5 are discussed herein. In the construction of FIG. 5, the base 130 includes a first base portion 130a and a second portion 130b. The first base portion 130a is coupled to the first glass member 150 via optical glue or another suitable adhesive. The first base portion 130a includes one or more angled walls 166, 170 and a recess 186. Together, the first base portion 130a and the first glass member 150 define an opening or reservoir. The second base portion 130b in positioned within and removal from the opening. The second base portion 130b includes an angled side 189 and the bore 146. When the second base portion 130b is positioned within the opening, the angled side 189 is parallel to the walls 166, 170 and the bore 146 is aligned with the recess 186. The transducer 14 is positioned within the bore 146 and supported by the recess 186. The second glass member 174 is positioned between the angled walls 166, 170 and the angled side 189 of the second body portion 130b. The second glass member 174 is positioned at a 45 degree angle, although other suitable angles are possible, as discussed above. Whereas the GSW combiner 10B of FIGS. 4A and 4B includes two reservoirs 154, 158, the GSW combiner 10B of FIG. 5 includes three reservoirs 154, 158, 190. That is, when the second body portion 130b is positioned within the opening 190, three reservoirs 154, 158, 190 are created. As shown, a third reservoir 190 is positioned on an opposite side of the body 130 from the second reservoir 158, and the aperture 146 containing the transducer 14 and the first reservoir 154 are positioned between second and third reservoirs 158, 190. In other or additional constructions, greater or few reservoirs may be created. For example, the GSW combiner may include up to 10 reservoirs. Additionally, the transducer 14, which has a diameter of 3 mm, was wrapped in a single layer (not shown) of parafilm and placed within an aluminum tube 194 having a diameter of 4 mm for water-proofing. In some constructions, other types of water-proofing may be used, such as a UV curing adhesive (e.g., manufactured by Thorlabs, Inc.s) or superglue. Like the construction of FIGS. 4A and 4B, a cover 102 containing the sample to be analyzed is positionable over the opening 138 and reservoir 154, as shown, during use. The GSW combiner 10B of FIG. 5 may be capable of up to 4× optical imaging due to an 8.8 mm thickness. The GSW combiner may be capable of up to 40× optical imaging, such as when paired with other objectives (e.g., long working distance objectives).

Figure 6:
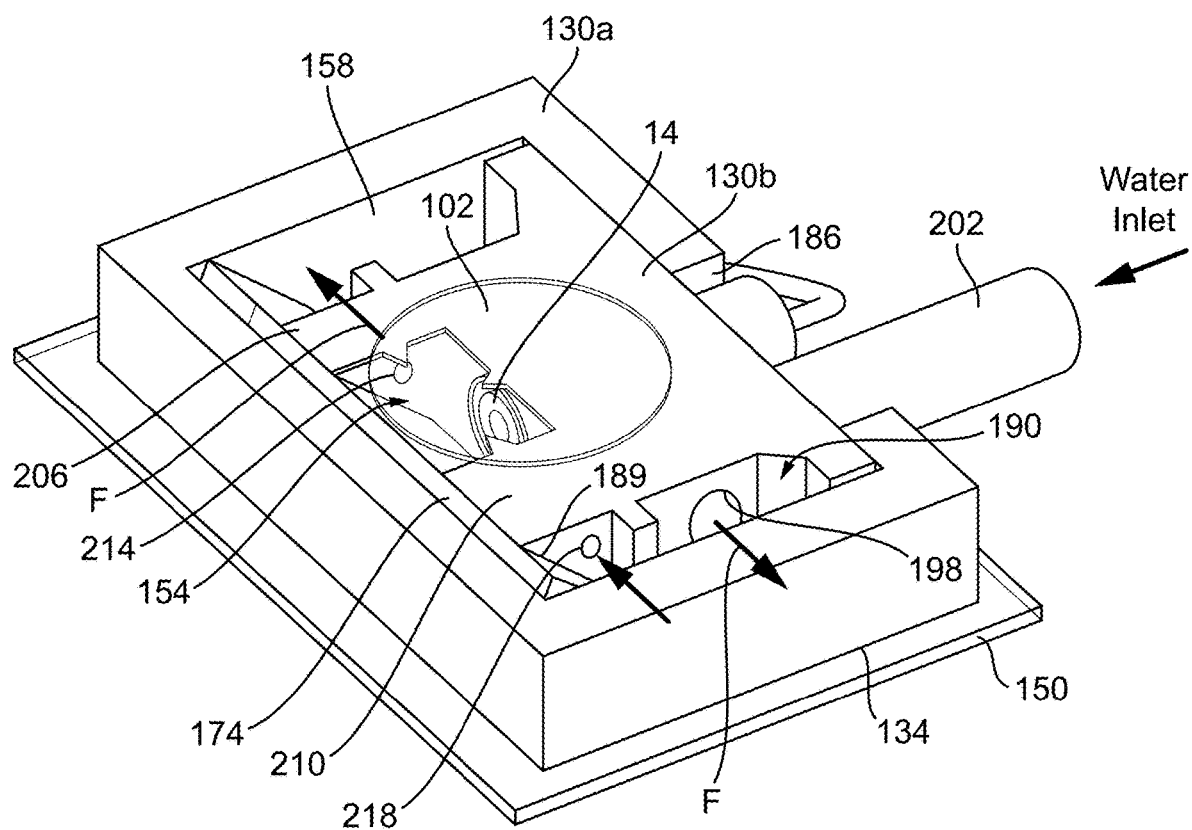
FIG. 6 illustrates rendering of a combiner according to another construction.

Another construction of a GSW combiner 10B is shown in FIG. 6. The combiner 10B of FIG. 6 is similar to that of FIG. 5, and only differences are discussed herein. As shown, the second body portion 130$b$ includes the bore 146 that receives the transducer 14 and the second body portion 130$b$ further includes a plurality of apertures. One of the apertures 198 has a portion that is parallel to the bore 146 and is in fluid communication with the third reservoir 190 (although in other constructions, the second aperture could be in fluid communication with the second reservoir). Accordingly, the second aperture 198 is essentially an L-shaped aperture. As shown, a tube 202 may be coupled to an inlet of the aperture 198. Additionally, in the construction of FIG. 6, the second body portion 130$b$ includes a first wall 206 that separates the first reservoir 154 from the second reservoir 158 and a second wall 210 that separates the first reservoir 154 from the third reservoir 190. As shown, each of the first and second walls 206, 210 include an aperture or bore 214, 218 extending therethrough to allow fluid communication among the reservoirs 154, 158, 190. Accordingly, water introduced into the body 130 (via the tube 212) moves along a flowpath F from the second aperture 198, to the third reservoir 190 to the first reservoir 154 (via the aperture 218 in the second wall 210), to the second reservoir 158 (via the aperture 214 in the first wall 206). A 60 mL syringe is used to inject the DI water into the second aperture 198. This configuration allows an easy and gentle influx of water in the event that water-levels drop. A valve (not shown) may be positioned in the first aperture or in the tube 202 to the water from flowing back into the syringe.

EXAMPLE

The illustrated constructions of the combiners 10A, 10B of FIGS. 2A-6 were constructed in SolidWorks 2018 and printed using a 3D printer (e.g., a Creality Ender-3) using 3D printing software (e.g., Ultimaker Cura 3.6.0). The bodies of each of the combiners 10A, 10B were printed using 1.75 mm polylactic acid (PLA, manufactured by, e.g., Hatchbox 3D) via a 0.06 mm extrusion and an 80% grid-style infill. In particular, the temperature setting of the extrusion was 210° C. followed by a heated bed at 68° C. The combiners 10A, 10B including bodies with multiple portions were printed with a different directionality of print to achieve a higher level of tolerance.

Experimental Analysis

Sample Preparation of 7.2 micrometer Thread Sample Slides

A 7.2 micrometer thread, cut around 10 mm, was placed running the diameter of a 12 mm micro cover glass slide. Placement was secured by the placement of two identical 0.5 mm×0.5 mm strips of electrical tape placed at opposite ends of the thread. A similar sample was constructed with a thread, cut around 5 mm, placed at an offset of 3 mm from the diameter. The thread offered both a clear optical and significantly photoacoustic target.

Sample Preparation of Black Tape Sample Slides

A square of black electrical tape, cut around 10 mm×10 mm, was placed on the center of a 12 mm micro cover glass slide. These were reused multiple times.

Optical Imaging

With renewed reference to FIG. 1 and as noted above, the respective combiner 10A, 10B was suspended over the objective 30 of an inverted microscope and secured by a V-clamp attached to a 3-axis stage. The combiner 10A, 10B was aligned by way of three 3D-printed guides extruded out of the platform and toward the center of the optical area, but sufficiently far away as to not influence signal propagation or line of sight, and the sample slide placed in focus. As the final combiner 10A, 10B was under 4.4 mm thick, the combiner 10A, 10B can be successfully used with the objectives having various magnifications and working distances. The working distance is the distance between the objective lens and the sample being imaged. At low magnifications, such as 4×, the working distance is relatively long (in some cases up to 30 mm). As the magnification is increased the working distance decreases. A 40× objective lens will typically have a working distance between 0.5 mm to 4 mm. Therefore, the combiners 10A, 10B may be successfully applied with objective lenses of a working distance of between 0.5 mm and 30 mm.

Raster Scanning

The fiber optic 22 or pulled fiber 26 was lined up from the opposite end by way of the micromanipulator 42 to move the light emission source vertically above a segment of the 7.2 μm thread. The light emission source was incrementally adjusted to a vertical distance of no more than 3 μm from the apex of the thread's diameter.

At such point, raster scanning was conducted through LABVIEW code controlling the micromanipulator 42 movements and obtaining transducer 14 signal. The 7.2 μm thread raster scans were taken at 1-micron steps. The black tape raster scans were taken at 100-micron steps. Data was averaged after 20 samples and analyzed through MATLAB R2016a code.

Results

Optical Sampling with 3D Model

A primary measurement of the combiner's 10A, 10B success is the ability to perform brightfield imaging as the goal is a combination of two modalities. As such, the combiners 10A, 10B were subjected to brightfield imaging with an inverted microscope. Images were recorded on the GPGP and GSW combiners 10A, 10B of 7.2 μm threads, which were placed on 12 mm sample cover slides positioned relative to the respective combiner 10A, 10B as described above. The images of FIGS. 7A and 7B recorded and listed here are those which were of the highest magnification that the GPGP combiner 10A of FIGS. 2A and 2B and the GSW combiner 10B of FIGS. 4A and 4B were capable of with an inverted microscope system.

Wave Propagation of GPGP and GSW

For contrast free imaging of cells, induced and recorded photoacoustic signals may be sufficiently small as to not get detected by a transducer 14. For this reason, the system most sensitive to photoacoustic signals is required. If a recorded signal is not sufficient for isolation, the approach cannot continue.

The combiners 10A, 10B of FIGS. 2A-2B and FIGS. 4A-4B were compared with each other as shown in FIG. 8 for the purpose of qualitative assessment. The photoacoustic signals were generated from the same sample across three different detection systems. To compare the signal reduction caused by the combiner 10A, 10B, the sample was placed directly on a 50 MHz transducer 14 and directly on the GPGP combiner 10A. Due to the large decrease in signal through the combiner 10A, a smaller combiner 10 using a 10 MHz transducer 14 was utilized. This resulted in a much larger photoacoustic signal, as shown in FIG. 8.

Determining Transducer Detection Area

Figures 9A, 9B, 9C:
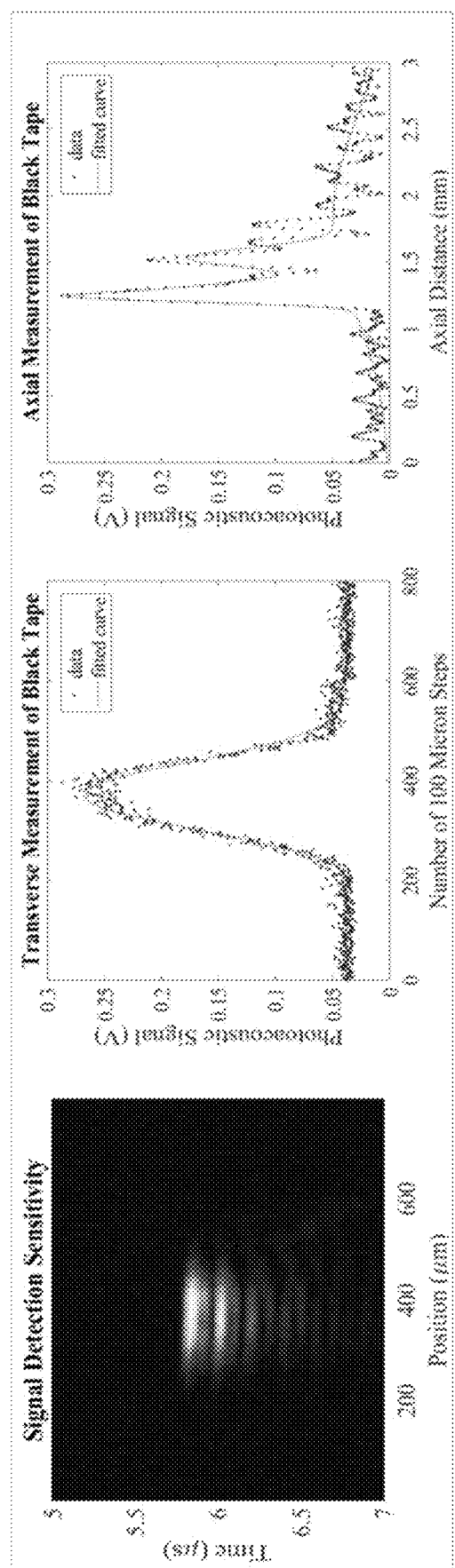
FIG. 9A illustrates a photoacoustic image reconstruction of a black tape sample using a GPGP combiner with a 10 MHz 6 mm transducer.
FIG. 9B illustrates vertical measurements of the black tape.
FIG. 9C illustrates transverse measurements of the black tape.

Black tape was scanned in order to measure the sensitivity across the GSW combiner 10B, as shown in FIGS. 9A-9C. Signal detection sensitivity and max signal per step were analyzed using MATLAB. The full width half maximum (FWHM) of the detection across the black tape was measured to be 1.5 cm.

Raster Scanning Comparison of GPGP and GSW Combiners

Both combiners 10A, 10B were tested through raster scanning of 7.2 μm thread. FIGS. 10A-10F show the reconstructed raster scan and data acquisitions for both the GPGP and GSW configurations of FIGS. 2A, 2B and 4A, 4B, respectively. The GPGP configuration of FIGS. 2A and 2B utilized a 50 MHz 6 mm transducer 14, and the GSW configuration of FIGS. 4A and 4B utilized a 10 MHz 3 mm transducer 14. The measurements in the transverse direction (e.g., those measurements going along the plane of the thread) and the axial direction (e.g., those of the vertical distance in direction of the pulse laser 18) were recorded.

Discussion

As shown above, the GPGP combiner 10A was capable of producing images with 4× magnification on an inverted microscope. This is important from the perspective that the combiner must be necessary to produce optical images. However, the GPGP combiner 10A has a minimum thickness of over 10 mm. Smaller optical prisms, too, would have introduced issues where insufficient material thickness was present to bend the wavelengths of light. However, as seen in the results of FIG. 7B, the GSW combiner 10B was usable with a magnification of 40×. This surpasses the optical capability of the GPGP combiner 10A. As noted above, however, the combiners 10A, 10B could be used with objectives having other magnifications and working distances.

This study compared the combiners 10A, 10B and the transducers 14 of the combiners 10A, 10B against one another for the purpose of qualitative assessment. When a 50 MHz transducer 14 was inserted into both the GPGP and GSW combiners 10A, 10B of FIGS. 2A-2B and 4A-4B to retrieve a reference signal, the GSW combiner 10B outperformed the GPGP combiner 10A. Furthermore, due to the nature of the GSW combiner 10B to effectively be shrunken down, a smaller 10 MHz transducer 14 was also compared to the 50 MHz from the GSW combiner 10B. This 10 MHz in the GSW combiner 10B, outperformed the 50 MHz in the GSW combiner 10B, both of which outperformed the 50 MHz GPGP combiner 10A. This is expected to arise from the different geometry of the GSW to the GPGP, as the GSW can run the signal through a decreased distance. More signal is preserved, and therefore the signal-to-noise ratio (SNR) is higher.

Black electrical tape is highly photoacoustic; thus, it has often been used as a positive control in photoacoustic microscopy. With black tape, an area corresponding to the max signal over a sample slide area could be analyzed. FIG. 9A is a photoacoustic image reconstruction of black tape using a GSW combiner 10B with a 10 MHz transducer 14. As indicated, the SNR is relatively high as it may be perceived in the reconstruction. In FIG. 9B, max signal per step, conducted in 100-micron steps, displays the signal as it would be perceived as if in a raster. Vertical measurements were also collected, with importance relating to the sample slide thickness or sample thickness. Results also relate to the frequency of the ultrasound transducer 14, as there is a negative relationship with wavelength and dissipation—longer wavelengths, as with the 10 MHz, are able to be discernable through a thicker media. In FIG. 9C, transverse measurements were obtained, which provide a reference for signal measurements as they correspond to a sample on the sample slide.

Both the combiners 10A, 10B of FIGS. 2A-2B and 4A-4B were utilized in raster scans of a photoacoustic 7.2 μm carbon fiber thread. Better resolutions correlate to better application to electrophysiology, so application of the combiners 10 to raster scanning was of special importance. Furthermore, all raster-scanning conducted was alongside optical observation, so this was an indirect application of the combination strength of the systems. As seen in FIGS. 10A, 10B the raster scan of the GSW combiner 10B was noticeably more consistent than the GPGP combiner 10A. In a comparison of vertical measurements (FIGS. 10E and 10F), the GSW combiner 10B displayed a noticeably sharper resolution. This carried over to the transverse measurements (FIGS. 10C and 10D) of the thread, where the GSW combiner 10B outperformed the GPGP combiner 10A with resolution capability. In all criteria observed, the GSW combiner 10B outperformed the GPGP combiner 10A in raster scanning.

In this study, several combiners 10A, 10B capable of simultaneous optical and photoacoustic imaging were developed and tested. The combiners 10A, 10B were configured to utilize the 40× optical zoom and signal acquisition by 3 mm ultrasound transducer 14. The combiners 10A, 10B were each a useful tool for a variety of standard photoacoustic microscopy studies. Compared to previous models, the ease of use would increase productivity and allow for further developments in the field. This would be especially useful as further, and more precise, generations will call for increasing levels of photoacoustic resolution and ever tighter level of system micromanipulation.

The first goal of this project was the comparison of performance between two different modalities: the GPGP and the GSW configuration. However, while SNR was of important consideration, other factors which influenced final development were that of the minimum viable combiner size and replicability of construction.

The capabilities of the experimental set-up could be upgraded. Further refinement may be possible with an alternate transducer, either with size or frequency. A change of transducer properties may provide an avenue for MHz optimization for use with future nearfield. Further combiner thinning may be achieved for improved utility with electrophysiology. Other potential improvements include, but are not limited to, automatic water-refilling and bed leveling.

While the final combiner is capable of achieving a novel combination, there were a few developments which did not improve the overall function yet should still be mentioned for their intended impact.

Pulled or Tapered Optical Fibers

An alternative configuration to FIG. 1 is to substitute the regular optical fiber 22 with a pulled (e.g., tapered) optical fiber or micropipette 26.

In optical microscopy, the smallest spot size possible when using conventional lenses, is limited by the diffraction limit of light. This determines the overall optical resolution of the images being produced. Diffraction limited resolution can be overcome by utilizing a miniature probe with a diameter smaller than that of the diffraction limited spot size. Light exiting the tip of the miniature probe has been shown to be the same size as the probe itself, thus, enabling sub-diffraction limited resolution (see FIG. 12). The resolution may be proportional to the tip diameter and is typically less than 200 nm. This has been shown within the field of near-field scanning optical microscopy (NSOM). In this field continuous wave lasers are used.

The continuous wave laser may be replaced with a pulsed wave laser. This enables the generation of the photoacoustic effect at an extremely reduced spot size (sub-diffraction limited) thereby creating an entirely new form of microscopy with super resolution images. The photoacoustic effect is defined by the generation of acoustic waves due to thermoelastic expansion, caused by optical absorption. The resolution (noted above) of the resulting image may be on the order of scanning electron microscopy, without requiring an environmentally controlled chamber, or any highly specific equipment.

Figure 12:
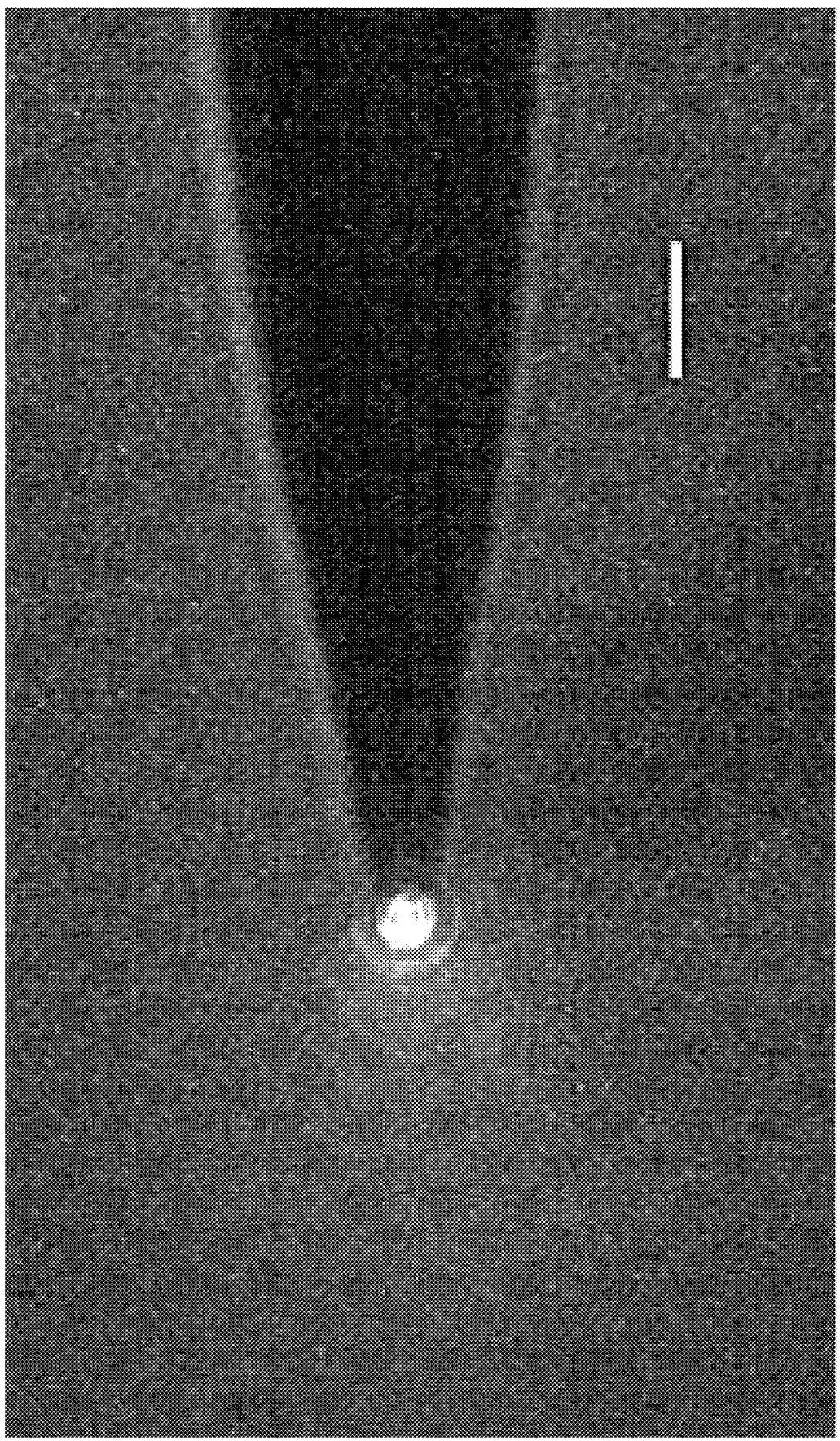
FIG. 12 illustrates an image of light exiting the tip of a miniature probe.

Pulsed lasers 18 introduced through pulled optical fibers 26 can create a photoacoustic effect at a spot size smaller than what currently exists—thus creating super resolution images. Accordingly, the pulled optical fiber 26 may be used for photoacoustic generation and photoacoustic imaging, sub-diffraction limited photoacoustic microscopy, and extremely high resolution imaging. The pulled optical fiber 26 is constructed by heating a regular optical fiber with a $CO_2$ laser (or otherwise), and pulling until the two ends part. This results in a tip 26' that measures tens to hundreds of nanometers in diameter. For example, in some constructions, the tip measures 20 mm to 1.5 microns in diameter. In other constructions, the tip measures less than 200 nm in diameter, which the typical diffraction limited spot size. Additionally or alternatively, the pulled fiber 26 may be coated with a reflective surface (e.g., gold, aluminum, titanium, copper, silver, etc.), which may help the pulsed light (or continuous wave) propagate the entire length thereof, and out its sub-diffraction-limited size tip 26'. The tip 26' of the pulled optical fiber 26 can be positioned tens of nanometers from the sample (biological or otherwise) being imaged. With reference to FIG. 12, pulsed light at a single point will generate the photoacoustic effect, resulting in a 1D photoacoustic reconstruction of the sample.

By taking a series of these 1D acquisitions, a 2D reconstruction of the sample can be created. This 2D reconstruction across the region of interest can be created in two different ways. The first way is by moving the tip of the pulled optical fiber covering the entire 2D surface. The second way is by moving the sample covering the entire 2D surface. This 2D reconstruction is in essence a raster scan, which is discussed above, of the surface or deeper within the sample, depending on the specific transducers 14, laser 18 power, and diameter of the pulled optical fiber tip 26, 26'. As noted above, sound will be detected by the transducer 14.

Figure 11:
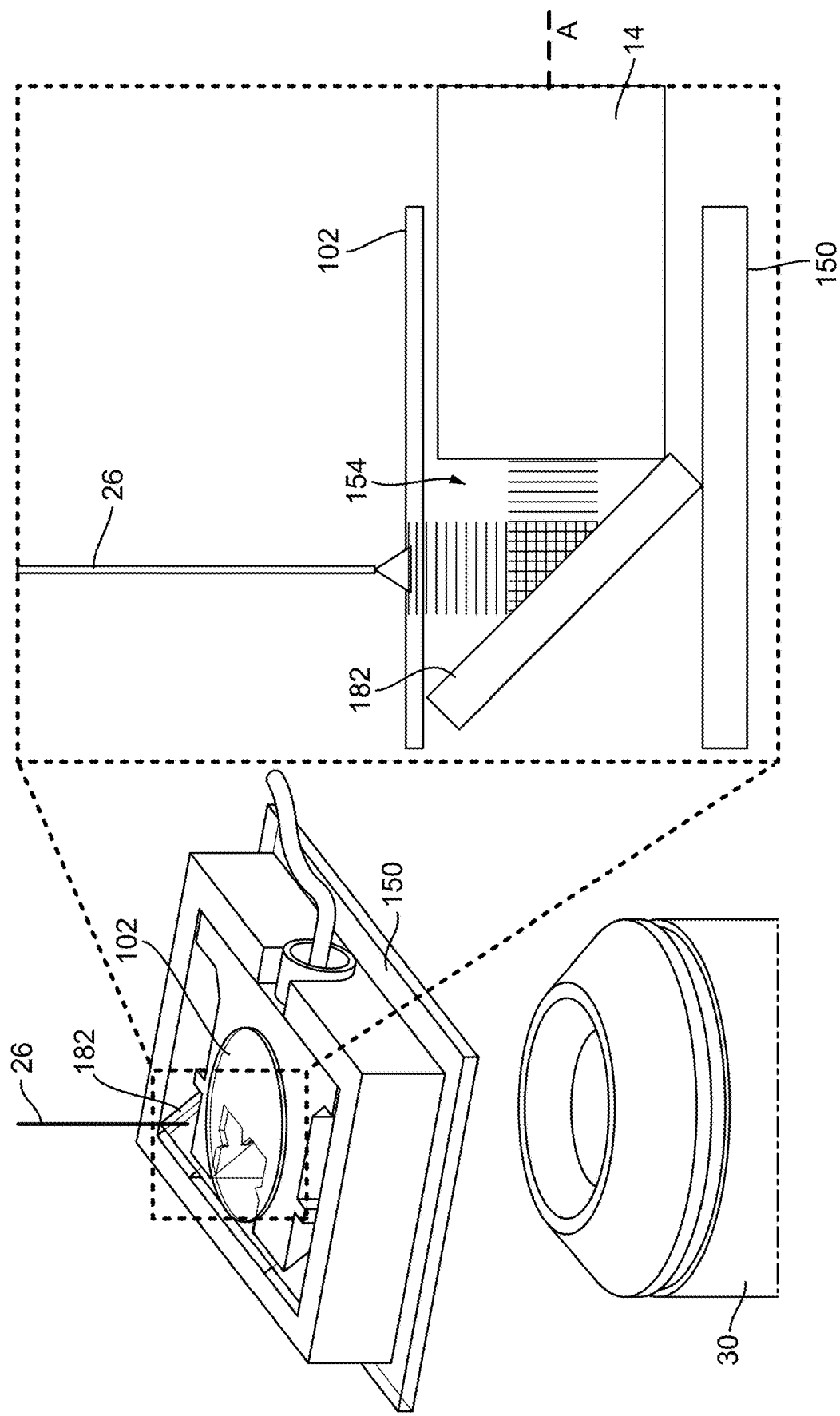
FIG. 11 is a schematic of a system for generating a photoacoustic image of a sample using a pulsed wave laser.

These sound waves can be detected in a number of ways, including but not limited to the positioning of transducers 14 or piezoelectric crystals. The pulled optical fiber 26 can be used as shown in FIG. 11, with the transducer 14 positioned on one side of the sample. Alternatively, the transducer 14 may be positioned below sample (e.g., on an opposite side of the sample from the pulled optical fiber 26, above sample (e.g., adjacent to and on the same side of the pulled optical fiber 26), at far end of the pulled optical fiber 26 (e.g., where both light and sound travel through the pulled optical fiber 26), in a ring around the pulled optical fiber 26 (e.g., as a ring transducer 14 with the pulled optical fiber 26 threaded through the transducer 14), or in an array surrounding the sample (e.g., ring transducer 14 surrounding the sample, e.g., tomography). Additionally, the pulled optical fiber 26 may be utilized as an optical and acoustic waveguide.

Although the present subject matter has been described in detail with reference to certain preferred constructions, variations and modifications exist within the scope of one or more independent aspects of the present subject matter, as described.

What is claimed is:

1. A photoacoustic and optical microscopy combiner, the combiner configured to support an ultrasound transducer defining an axis, the photoacoustic and optical microscopy combiner comprising:
   a body including a base and an opening extending through the base; and
   a glass member at least partially positioned within the opening, the glass member including a surface positioned at an angle relative to the base and the axis of the transducer;
   wherein the body is configured to support a sample slide such that the sample slide is at least partially over the opening and positioned between an output of a laser and the glass member, and
   wherein the sample slide is positioned such that a sample on the sample slide is configured to receive light from the output of the laser and redirect acoustic waves to the ultrasound transducer to generate a real-time image of a sample, and
   wherein the body is coupled to a transparent support member, the body further including a first reservoir created by the opening and the transport support member, a second reservoir positioned adjacent to and in fluid communication with the first reservoir and an angled wall defining a plane that is parallel to the face of the glass member, the angled wall configured to at least partially support the glass member, the body configured to receive water in the first reservoir and the second reservoir at a depth sufficient to submerge the glass member.

2. The photoacoustic and optical microscopy combiner of claim 1, wherein the angle is 45 degrees.

3. The photoacoustic and optical microscopy combiner of claim 1, wherein the body is configured to receive water at a depth sufficient to submerge the glass member.

4. The photoacoustic and optical microscopy combiner of claim 1, wherein the glass member is a first glass member and further comprising a second glass member positionable within the opening, the second glass member including a face that is oriented parallel to the face of the first glass member.

5. The photoacoustic and optical microscopy combiner of claim 1, wherein the body includes a handle for suspending the combiner above an objective of a microscope.

6. The photoacoustic and optical microscopy combiner of claim 1, wherein the real-time image represents a 40 times zoom of the sample.

7. The photoacoustic and optical microscopy combiner of claim 1, wherein the body is configured to support the sample slide such that the sample slide is positioned adjacent to the sample on the sample slide.

8. A photoacoustic and optical microscopy combiner, the combiner configured to support an ultrasound transducer defining an axis, the photoacoustic and optical microscopy combiner comprising:
   a transparent support member,
   a body coupled to the transparent support member and including a base, an opening, and a first reservoir created by the opening and the transparent support member, a second reservoir positioned adjacent to and in fluid communication with the first reservoir, and an angled wall defining an angled surface, the angled surface oriented at a 45-degree angle relative to the base and the axis of the transducer; and
   a glass member positionable within the body and at least partially supported by the angled surface and at least partially within the opening, the glass member including a face that is oriented parallel to the angled surface,
   wherein the body is configured to support a sample slide such that the sample slide is at least partially over the opening and positioned between an output of a laser and the glass member, and
   wherein the sample slide is positioned such that a sample on the sample slide is configured to receive light from the output of the laser and redirect acoustic waves to the ultrasound transducer to generate a real-time image of a sample, and
   wherein the body is configured to receive water in the first reservoir and the second reservoir at a depth sufficient to submerge the glass member.

9. The photoacoustic and optical microscopy combiner of claim 8, wherein the body is configured to support the sample slide such that the sample slide is positioned adjacent to the sample on the sample slide.

* * * * *